(12) United States Patent
Gamache

(10) Patent No.: US 10,428,960 B2
(45) Date of Patent: *Oct. 1, 2019

(54) VALVE WITH A LOAD VARYING MECHANISM, AND METHOD OF OPERATING THE SAME

(71) Applicant: Mécanique Analytique Inc., Thetford-Mines (CA)

(72) Inventor: Yves Gamache, Adstock (CA)

(73) Assignee: APN-AFP INC., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/231,149

(22) Filed: Aug. 8, 2016

(65) Prior Publication Data

US 2016/0348795 A1 Dec. 1, 2016

Related U.S. Application Data

(63) Continuation of application No. 14/420,180, filed as application No. PCT/CA2013/050594 on Jul. 31, 2013, now Pat. No. 9,435,440.

(Continued)

(51) Int. Cl.
*F16K 5/16* (2006.01)
*F16K 3/18* (2006.01)
(Continued)

(52) U.S. Cl.
CPC ............... *F16K 5/161* (2013.01); *F16K 3/10* (2013.01); *F16K 3/18* (2013.01); *F16K 5/166* (2013.01); *F16K 5/201* (2013.01); *F16K 11/0743* (2013.01); *F16K 11/0833* (2013.01); *F16K 11/0873* (2013.01); *F16K 31/602* (2013.01); *F16K 37/0041* (2013.01);
(Continued)

(58) Field of Classification Search
USPC ................ 251/160, 161, 180, 181, 188
See application file for complete search history.

(56) References Cited

U.S. PATENT DOCUMENTS

| | | | |
|---|---|---|---|
| 2,449,733 A * | 9/1948 | Wilkening | F16K 5/162 137/625.11 |
| 3,297,053 A | 1/1967 | McKinney | |

(Continued)

FOREIGN PATENT DOCUMENTS

| | | |
|---|---|---|
| DE | 10 2004 063 270 A1 | 7/2006 |
| EP | 2056005 A2 | 5/2009 |

(Continued)

*Primary Examiner* — John Fox
(74) *Attorney, Agent, or Firm* — Price Heneveld LLP

(57) ABSTRACT

A valve is provided. The valve includes a body provided with fluid passages for circulating fluid therein. The body has a body interface with ports connected to the fluid passages. The valve also includes a valve element having a valve element interface facing the body interface. The valve element can move between different positions so as to permit or obstruct communication between the fluid passages. A biasing element biases the valve element interface against the body interface. A load varying mechanism is provided to load the biasing element with different sealing load forces according to the different positions of the valve element. The sealing load force applied on the rotor is thus decreased during rotation, reducing friction between the valve body and the valve element.

18 Claims, 28 Drawing Sheets

Related U.S. Application Data

(60) Provisional application No. 61/679,971, filed on Aug. 6, 2012.

(51) Int. Cl.
*F16K 11/074* (2006.01)
*F16K 3/10* (2006.01)
*F16K 5/20* (2006.01)
*F16K 11/087* (2006.01)
*F16K 11/083* (2006.01)
*F16K 31/60* (2006.01)
*F16K 37/00* (2006.01)
*G01N 30/32* (2006.01)

(52) U.S. Cl.
CPC ....... *G01N 30/32* (2013.01); *G01N 2030/328* (2013.01); *Y10T 137/0318* (2015.04)

(56) References Cited

U.S. PATENT DOCUMENTS

| | | |
|---|---|---|
| 3,640,310 A | 2/1972 | Erlich |
| 4,550,742 A | 11/1985 | Stearns |
| 4,867,414 A | 9/1989 | Hubacek |
| 6,098,646 A | 8/2000 | Hennemann et al. |
| 6,193,213 B1 | 2/2001 | Stearns et al. |
| 6,378,841 B1 | 4/2002 | Russell |
| 6,453,946 B2 | 9/2002 | Nichols et al. |
| 6,643,946 B1 | 11/2003 | Schuh |
| 7,377,291 B2 | 5/2008 | Moon et al. |
| 7,503,203 B2 | 3/2009 | Gamache et al. |
| 8,272,401 B2 | 9/2012 | McLean |
| 8,322,374 B2 * | 12/2012 | Tomita ............... G01N 30/20 137/625.11 |
| 2010/0059701 A1 | 3/2010 | McLean |
| 2010/0090146 A1 | 4/2010 | Keeper et al. |
| 2010/0200078 A1 | 8/2010 | Timko et al. |
| 2012/0119127 A1 | 5/2012 | Tower |
| 2012/0181466 A1 | 7/2012 | Gamache et al. |
| 2014/0053910 A1 * | 2/2014 | Bunner ............... F16K 3/10 137/1 |

FOREIGN PATENT DOCUMENTS

| | | |
|---|---|---|
| EP | 2341269 A1 | 7/2011 |
| JP | H 04-29382 | 12/1993 |

* cited by examiner

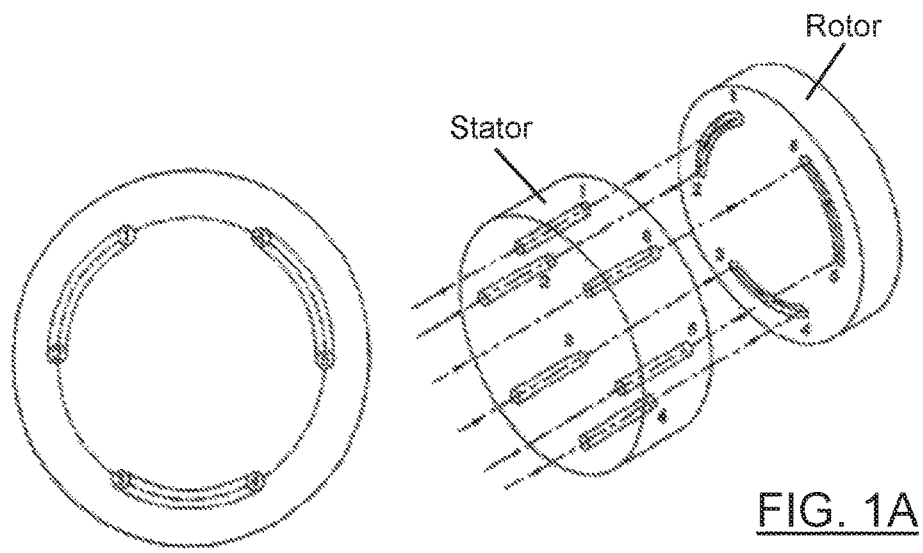
FIG. 1B
(PRIOR ART)
FIG. 1A
(PRIOR ART)
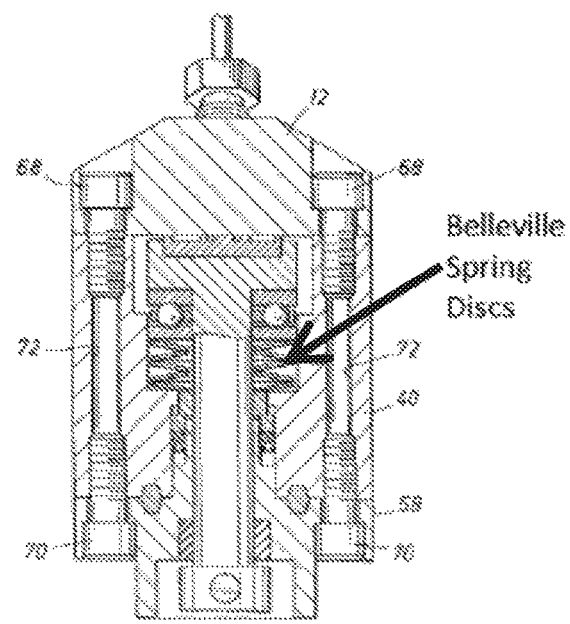
FIG. 2
(PRIOR ART)

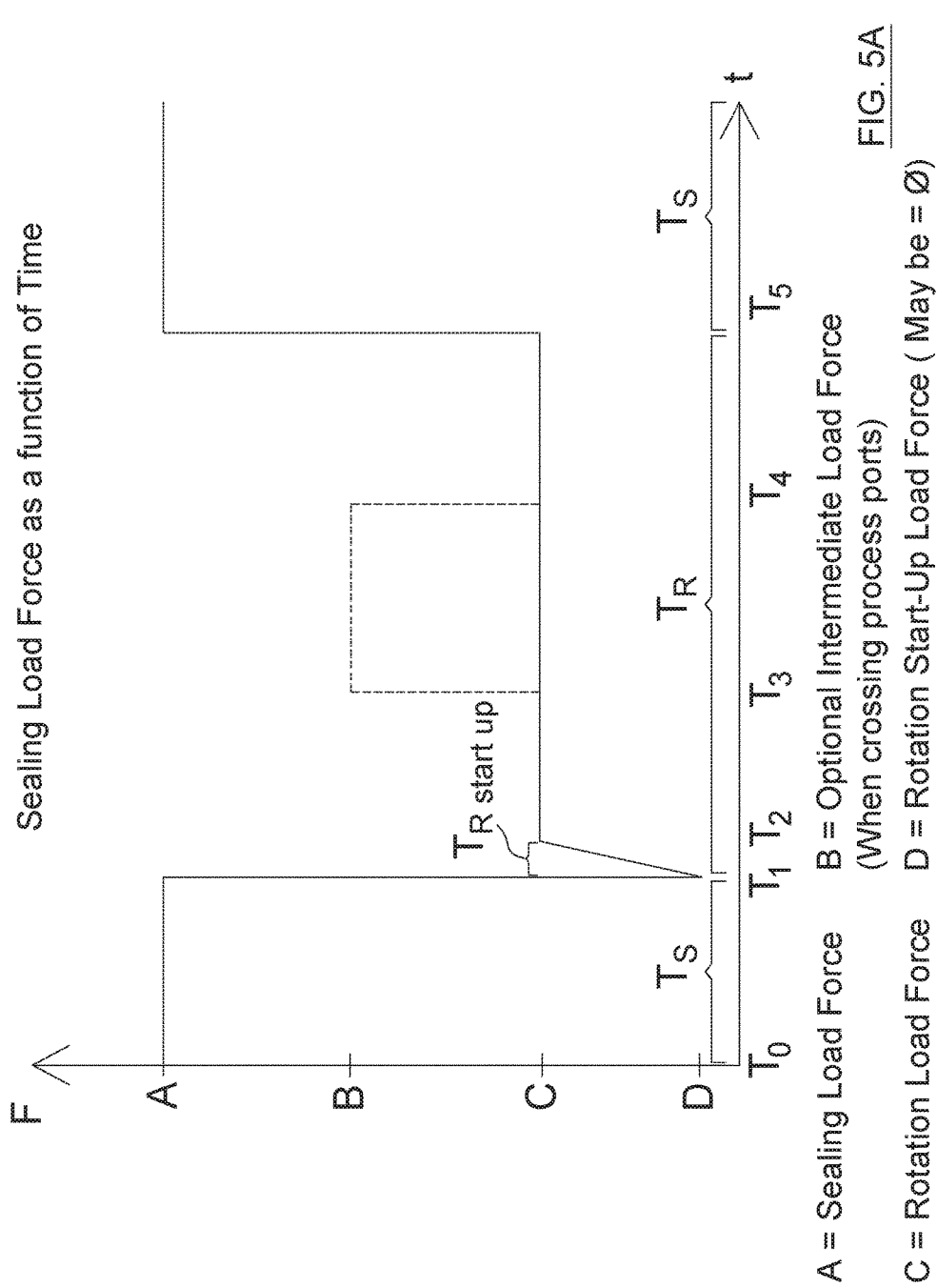

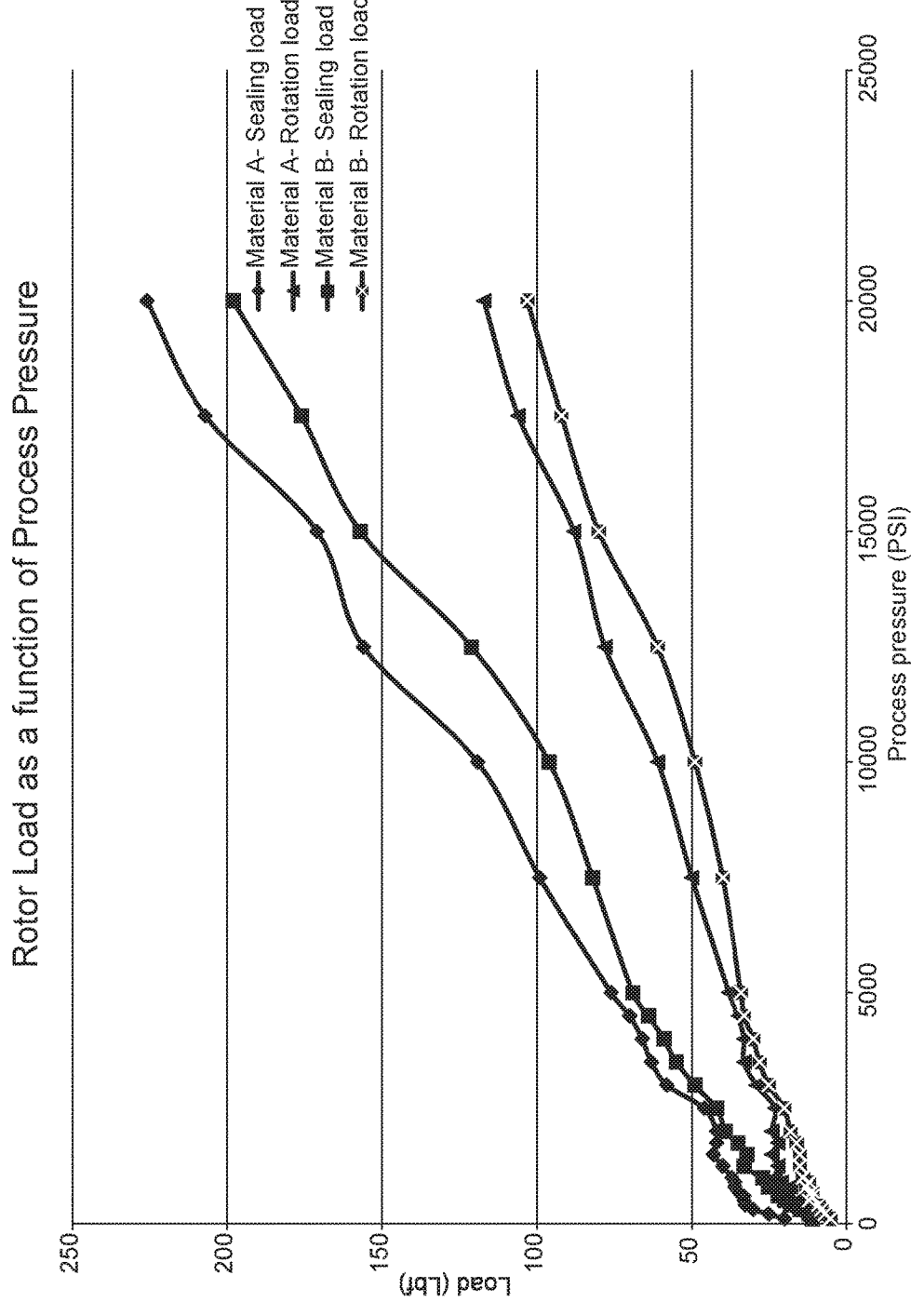

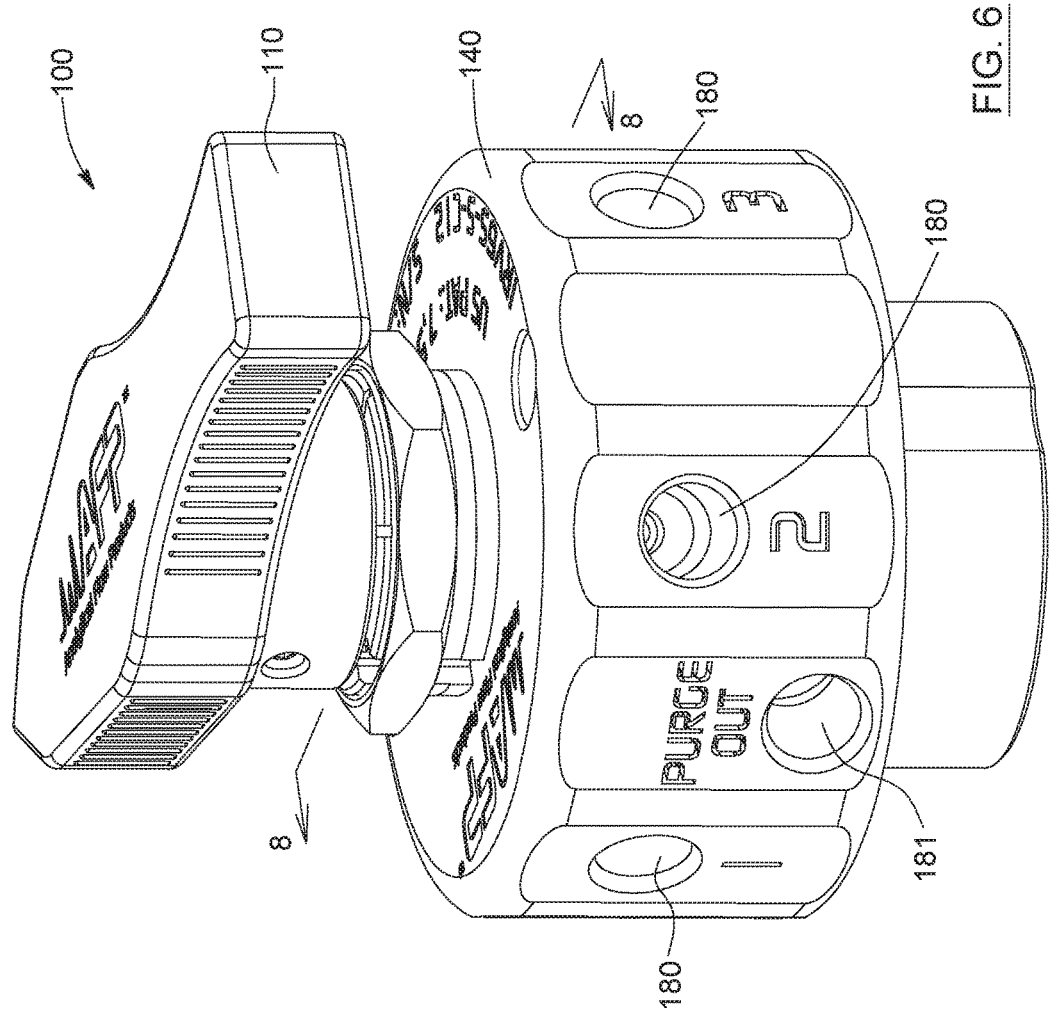

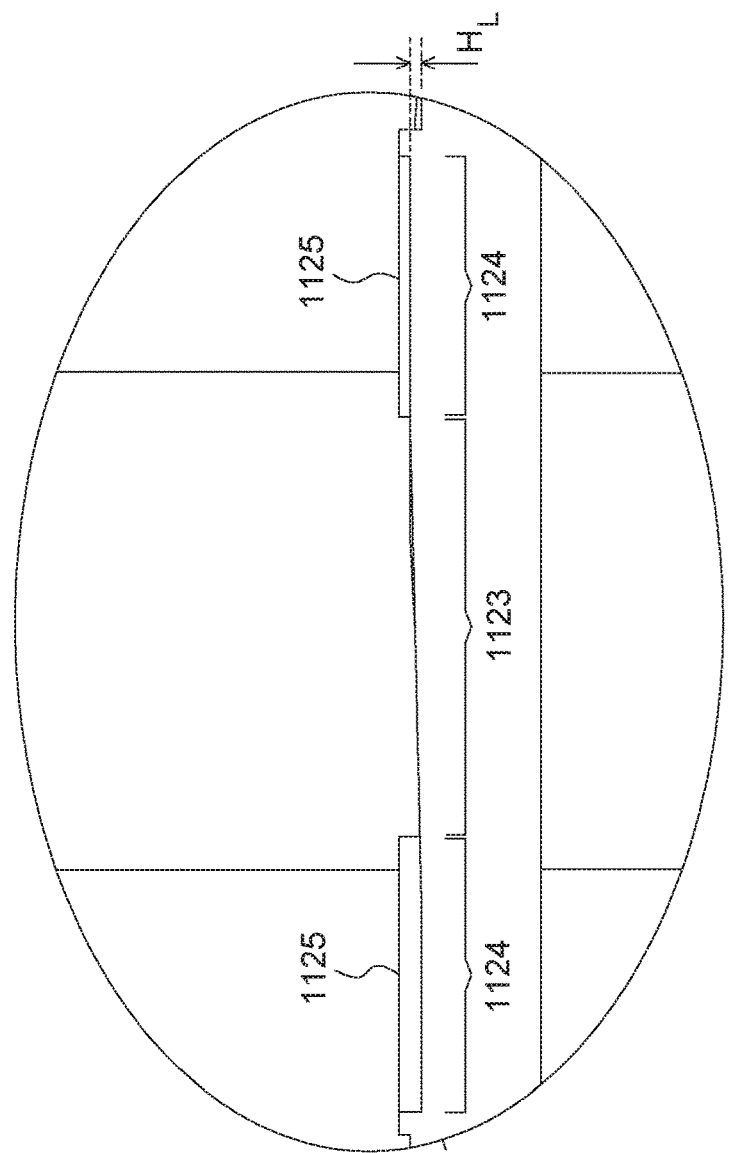
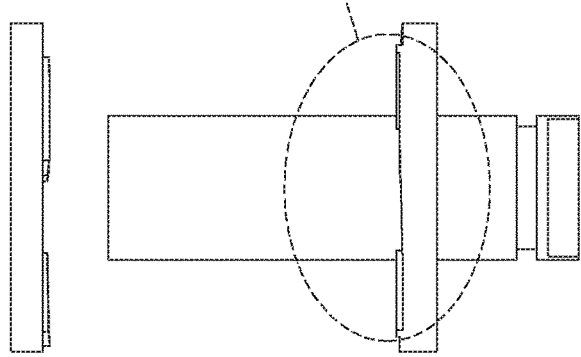
FIG. 14D
FIG. 14C

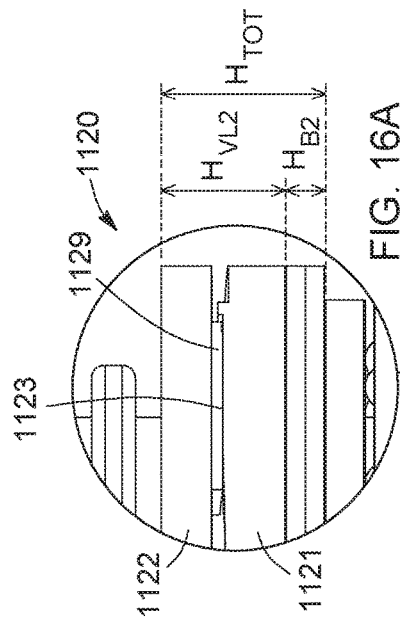
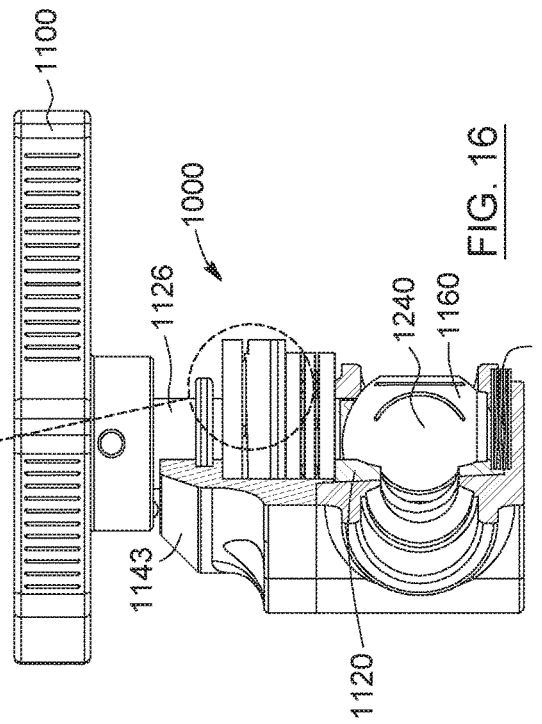
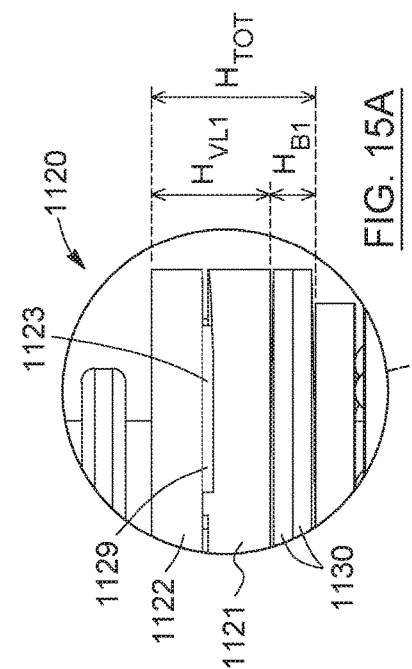
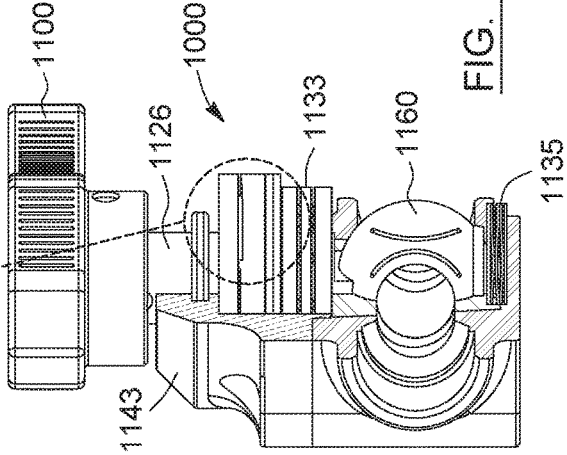

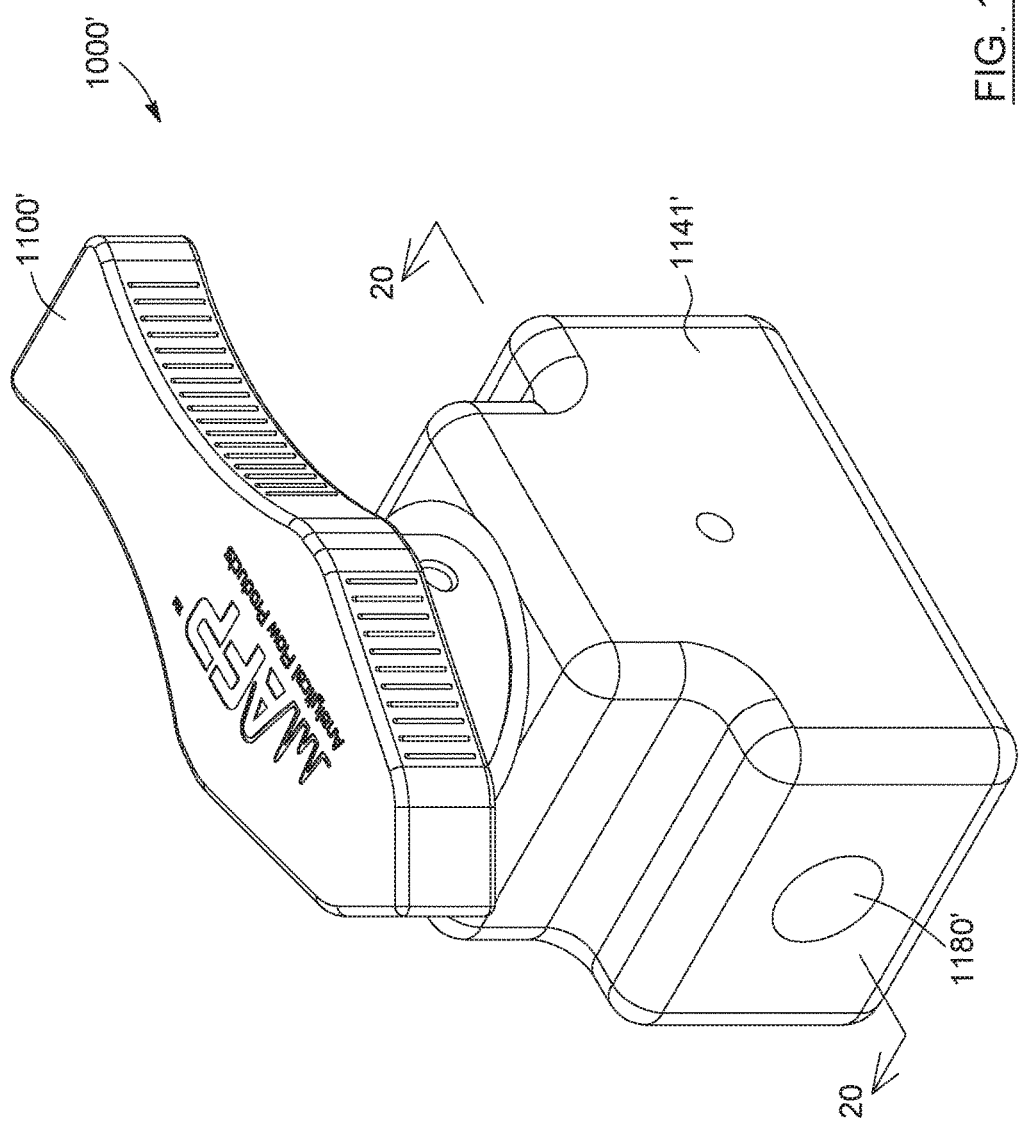

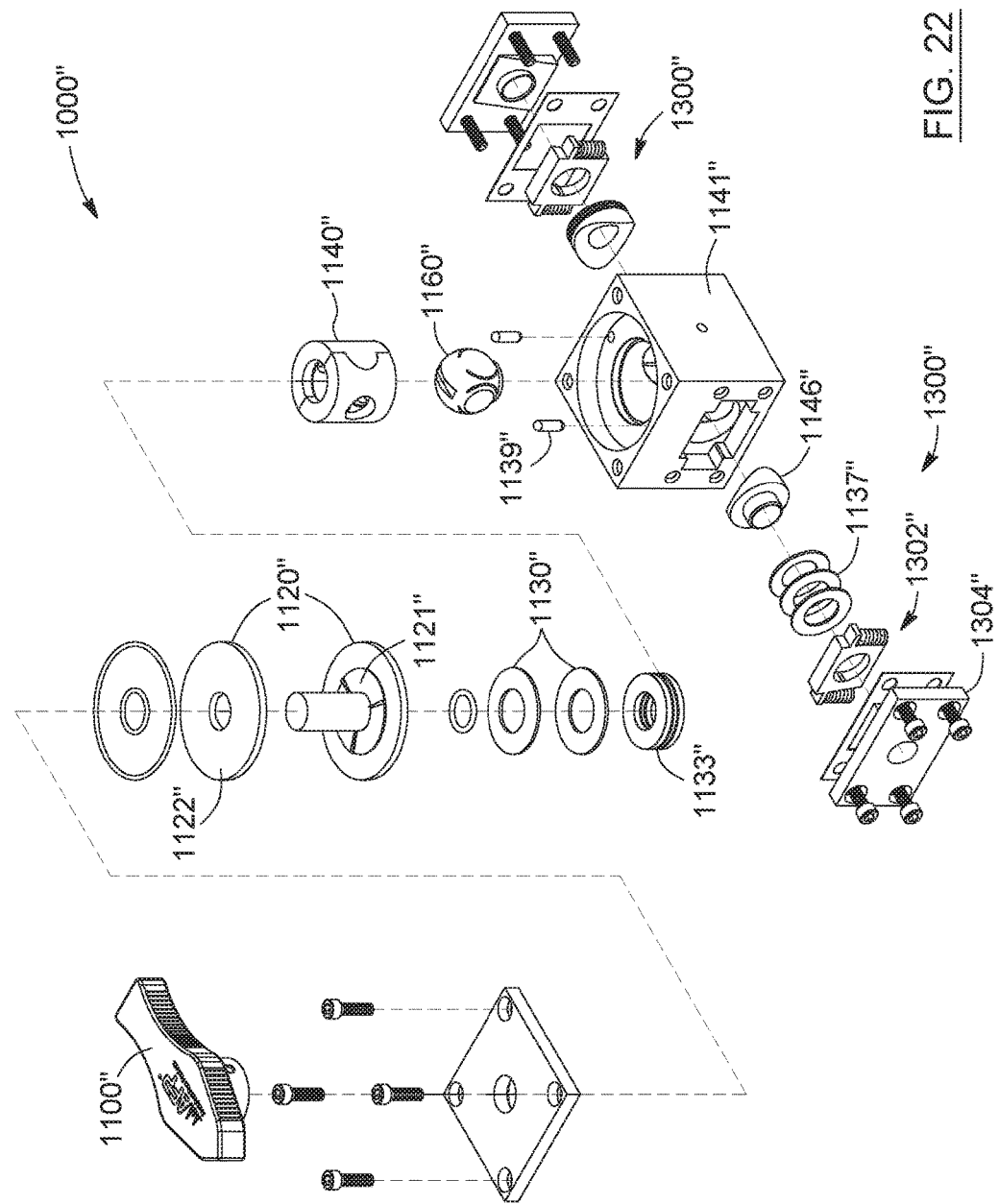

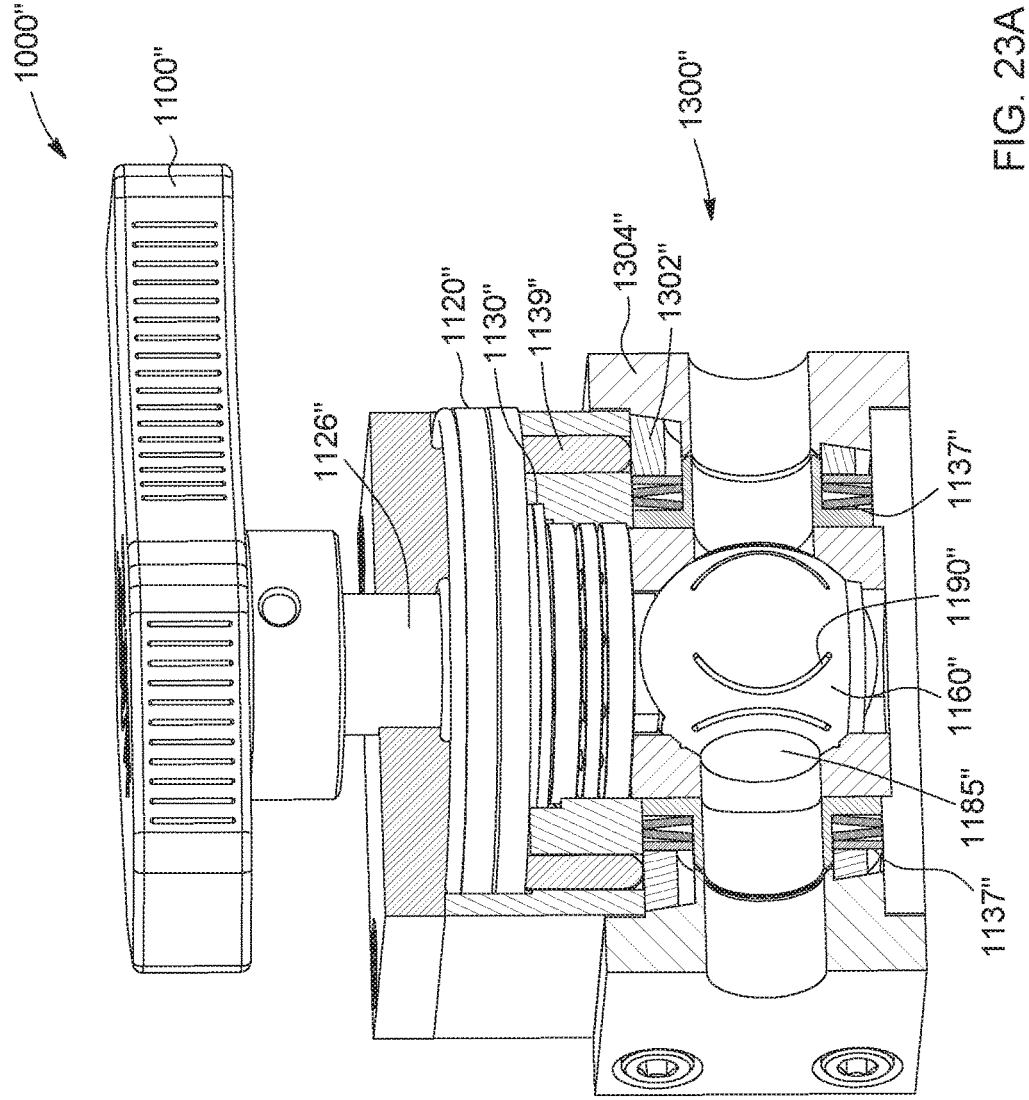

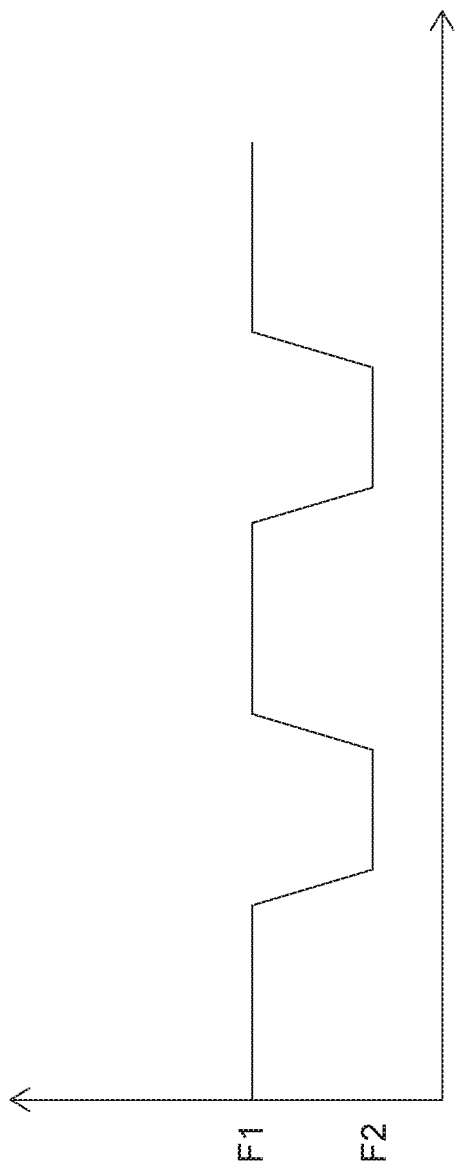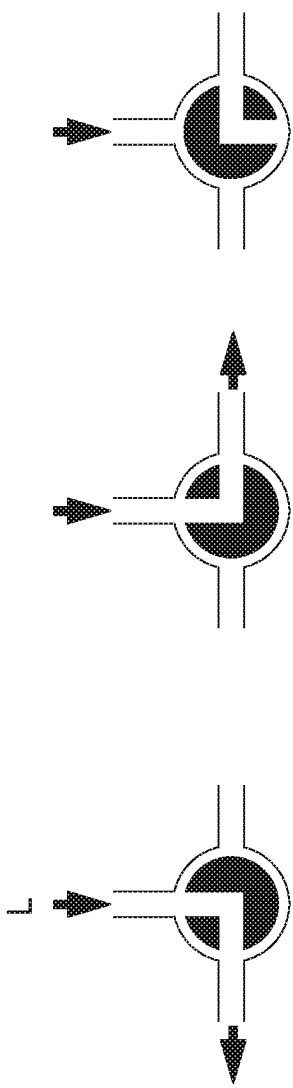
FIG. 25B

VALVE WITH A LOAD VARYING MECHANISM, AND METHOD OF OPERATING THE SAME

FIELD OF THE INVENTION

The present invention generally concerns systems and methods related to valves and more particularly relates to a valve with a load varying mechanism and a method for reducing friction during movement of a valve element.

BACKGROUND

Liquid chromatography and auto-sampler systems rely mostly on flat rotary based design valves to handle various fluids. Many different configurations are possible, such as the standard six-port injection valves, valves with syringe port or for sample stream selection, column selection, multi-position/multitask, such as loading, injecting, washing, etc. In most cases, valves have a flat rotor and a flat stator. The flat rotor is pushed against a fixed flat stator. The rotor has various grooves machined in it, allowing different stator port connection schemes to fit any particular application.

To exemplify the description of such a prior art valve system, we will refer to a typical six-port liquid chromatographic valve. Such valve is shown in FIGS. 1A to 2. This technology has been used for more than half a century. The sealing, i.e. the leak integrity, between two adjacent ports and all outboard leaking integrity from any port, is provided by applying a load on the rotor, such required load being greater for higher pressure operations. The load, or pressing force, is normally set by a mechanical biasing element, such as a compression spring or a stack of Belleville discs. Since the force maintaining the rotor on the stator is relatively high, so is friction and resultant wear. Because wear occurs when the rotor is turned against the stator, the lifetime of such a valve is short. Scratches eventually appear on the rotor, which is usually made of softer material than the stator.

Friction between the rotor and the stator causes particles to be generated, further increasing the problems associated with wear. Leaks are likely to appear, and eventually the valve will have to be repaired or replaced. This problem may be found in most flat and conical rotary valves available.

Referring to FIG. 3, from U.S. Pat. No. 6,643,946 pertaining to Rheodyne, a rotor and a stator of a typical flat rotary valve are shown, both presenting scratches resulting from friction and wear. In order to increase the lifetime of rotary valves, U.S. Pat. No. 6,453,946 discloses a valve in which one of the sealing surfaces is coated with Tungstene Carbide/Carbon (WC/C) while the other sealing surface is provided with a fluorocarbon polymer.

In Ultra High Performance Liquid Chromatography (UHPLC) applications, the process pressure can be as high as 20,000 PSI. By "process pressure" it is meant the pressure of the fluid circulating in the valve, such as the sample gas, carrier gas or liquid mobile phase. At such a pressure level, the required rotor loading force provided by the biasing element is high, and so is friction and resultant wear. Although coating the sealing surfaces of the stator may improve the lifetime of the rotary valve, there is a still a need for an improved valve system that may allow even longer lifetime, especially for high pressure applications.

Also known are the following references: U.S. Pat. Nos. 3,297,053; 3,640,310; 6,193,213; 6,453,946; 7,503,203; and US Patent application 20100059701.

In U.S. Pat. No. 6,193,213, the process fluid is used for applying an additional load force on the rotor. The load force is therefore a function of the process pressure, which is generally constant. As a result, the overpressure on the rotor is also constant and equally applied whether the rotor is stationary or rotating, which disadvantageously does not allow the load force to be varied. A further disadvantage may result from using the process fluid within different sections of the valve because this increases the risk of contaminating the fluid. Additional seals are then required to properly seal the different valve sections.

Another problem arises from the fact that valves are usually tuned at ambient temperature, but are mostly used at different temperatures, from cryogenic temperatures to temperatures of around 350° C. The behavior of each part of the valve may therefore differ greatly depending on the temperature range at which it is operated. Consequently, a valve can work perfectly when tuned and operated at ambient temperature, but important leakage may occur when the valve is used in a system operated at a different temperature.

In light of the above, there is also a need for an improved valve, or an improved system for varying the load applied on the valve element of a valve. There is also a need for a method of operating a valve that would help reduce friction between the movable valve element and the stationary body of the valve.

SUMMARY OF THE INVENTION

According to an aspect of the present invention, a valve is provided. The valve includes a body provided with fluid passages for circulating fluid therein at a fluid pressure. The body has a body interface with ports connected to the fluid passages. The valve also includes a valve element having a valve element interface facing the body interface, the valve element interacting with the ports of the body interface. The valve element is movable between different positions so as to permit or obstruct communication between the fluid passages. The valve includes an actuating mechanism for moving the valve element between the different positions. The valve includes a biasing element configured to bias the valve element interface against the body interface with a sealing load force. The valve includes a load varying mechanism configured to variably load the biasing element based on the different positions of the valve element, the biasing element thereby applying different sealing load forces on the valve element based on the different positions.

In one implementation, the valve is a rotary valve, the valve element is a rotor, and the body is a housing, the rotor being mounted in the housing. The actuating mechanism is a rotary driver for rotating the rotor. The biasing element applies a sealing load force on the rotor. The load varying mechanism allows applying different load forces on the rotor based on the different positions of the rotor. When the valve is stationary, the biasing element applies the process sealing load force having predetermined value. When the valve is rotating, the sealing load force applied in reduced to a rotation load force, smaller than the sealing load force.

In yet another implementation, the rotary valve is a conical rotary valve. The valve element has a frustro-conical body. The frustro-conical body is provided with at least one channel, which extends within the body or at its surface, for placing the different ports of the housing in fluid communication.

In yet another implementation, the rotary valve is a ball-valve. The valve element is a ball, and the body with the passages is a packing surrounding the ball. The ball is provided with a through hole which allows putting the passages in fluid communication, or the block them, according to the ball position.

In yet another implementation, the load varying assembly includes a controller, and a motor for varying the height, and therefore the compression of the biasing element. Preferably, the valve comprises or is used in combination with a second, actuating motor to actuate the valve element. As an example, the valve can be a sample stream selection valve, in which the controller is used to further vary the sealing load force when crossing over ports, by applying a sealing force having a value between the process sealing force value and the movement load force value. Preferably, the motors are electrical motors.

In one implementation, the load varying mechanism includes a position detector to determine the position of the valve element. The load varying mechanism can also include a loading force detector, to determine the pressure or sealing load force applied by the biasing element.

In one implementation, the load varying assembly includes a fixed member and a movable member, the movable member being operatively linked to the actuating mechanism and/or rotor and to the biasing element. When the actuating mechanism moves the valve element between different positions, the movable member of the load varying mechanism also moves, thereby compressing or decompressing the biasing element. Decompressing the biasing element reduces the sealing load force applied on the valve element when it moves, thereby reducing friction in the valve.

In one implementation, the fixed and movable members are cam washers having alternating convex and concave portions. The cam washers are positionable in sealing and rotation configurations. When placed in the sealing configuration, the convex portions of the cam washers are aligned, increasing a height the cam washer assembly, which compresses the spring biasing elements to apply a sealing load force on the valve element. When placed in the rotation configuration, the convex and concave portions are gradually interlocking, reducing the height of the cam washer assembly, which decompresses the biasing element, applying a load force smaller than the sealing load force.

According to another aspect of the invention, a method for channeling a fluid through different passages of a valve is provided. The method comprises a step of loading the biasing element of the valve with different sealing load forces as the valve element moves to different positions.

In one implementation, the method comprises the steps of: a) applying a sealing load force on the valve element when the valve element is stationary and the valve is in operation, and b) applying a reduced sealing load force on the valve element when the valve element is moved.

In one implementation, the method comprises a step performed prior to step b), of applying a start-up load force on the valve element, the start-up load force being smaller than the reduced sealing load force applied when the valve element is moving between to positions. In one implementation, the start-up load force is 0.

In one implementation, the method comprises a step performed after step b), of applying an intermediate sealing load force on the valve element, the intermediate load force being smaller than the process sealing load force, but greater than the rotation load force. For example, this method can be applied in a sample stream selection valve when crossing over a port.

An advantage of the present method and valve is that friction between the sealing surfaces of the valve element and stationary body of the valve is reduced during movement of the valve element, and preferably just before the movement start-up. Reducing the friction between the sealing surfaces when the valve element is moved reduces wear and particle generation in the valve, which in turn reduces leaks and/or contamination. Another advantage of the method is that the load force applied on the valve element is not dependent upon the operating pressure of the valve, as in U.S. Pat. No. 6,193,213.

Advantageously, the load varying mechanism also allows performing a cleaning/washing cycle without having to dismantle or disassemble the valve. Indeed, when reducing the valve element load to an intermediate cleaning load, a cleaning fluid can be applied to flow through the valve from a purge port, so as to clean all surfaces and grooves by moving the valve element; this intermediate cleaning load being low enough to allow a slight spacing of the valve element from the stationary body. This method is particularly adapted to rotary valve, in which the valve element, which is a rotor, can be rotated at high speeds.

Another advantage of this method and valve is that, when the valve element is stationary in an operational position, it is possible to apply a much higher load on the valve element than what is typically found in other commercially available valves, and this, without the risk of damaging the valve element. This results in a much higher sealing integrity.

The load varying mechanism also helps to maintain the same predetermined load scheme, even if some of the characteristics of the components change over time, such as can occur when the biasing element softens or the parts of the valve thermally expand in the case of high temperature applications.

Methods according to implementations of the invention can be used for flat, conical and ball-type rotary valves, among other possible valves.

Other features and advantages of the present invention will be better understood upon reading of preferred implementations thereof, with reference to the appended drawings.

BRIEF DESCRIPTION OF DRAWINGS

FIG. 1A is a side perspective view of a six-port liquid chromatographic valve known in the prior art, shown partially. FIG. 1B is a top view of a rotor forming part of the prior art valve shown in FIG. 1A.

FIG. 2 is a cross-section view of a liquid chromatographic valve known in the prior art.

FIG. 5A is a graph of the sealing load force applied on the valve element of FIG. 4, as a function of time, according to an implementation of the method. FIG. 5C is a graph of the load (in Lbf) as a function of the process pressure (in PSI), for two different materials used for the valve element.

FIG. 6 is a perspective view of a rotary valve, according to a second implementation of the invention.

FIGS. 14A, 14B and 14C are a top perspective view, a bottom perspective view and a side view, respectively, of two components of the rotary valve of FIG. 12. FIG. 14D is an enlarged view of a detail of FIG. 14C.

FIGS. 15 and 16 are partial side cross-section views of the rotary valve of FIG. 12, with the valve shown in different positions. FIGS. 15A and 16A are enlarged views of portions of FIGS. 15 and 16.

FIG. 17 is a perspective view of a rotary valve, according to a fourth implementation of the invention.

FIG. 22 is an exploded view of the rotary valve of FIG. 21.

FIG. 23A is a perspective view of the rotary valve of FIG. 21, with the stator shown in cross-section, in a configuration where the ball valve is moved.

FIGS. 25A and 25B are graphs of the load force applied on the rotor, according to different positions of the rotor, for a T-channel ball rotary valve, and for an L-channel ball rotary valve, the respective balls being shown in top view cross-sections.

Figure 3:
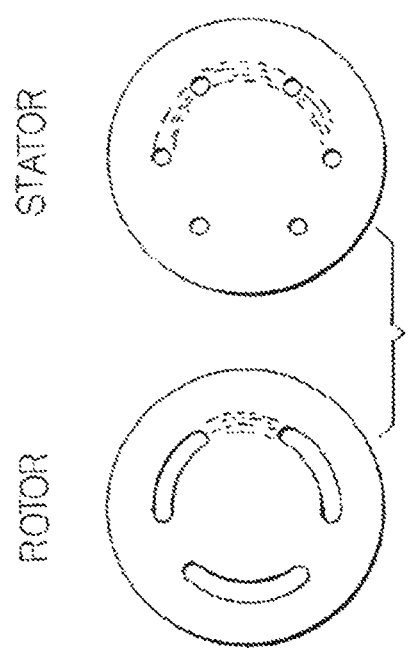
FIG. 3 is a top view of sealing surfaces of a rotor and a stator of prior art rotary valves, the sealing surfaces showing signs of wear.

While the invention will be described in conjunction with example implementations, it will be understood that it is not intended to limit the scope of the invention to such implementations. On the contrary, it is intended to cover all alternatives, modifications and equivalents as may be included as defined by the present application.

DETAILED DESCRIPTION OF PREFERRED IMPLEMENTATIONS OF THE INVENTION

Within the following description, similar features of the drawings have been given similar reference numerals. To preserve the clarity of the drawings, some reference numerals have been omitted when they were already identified in a preceding figure.

The implementations described below are given by way of example only and the various characteristics and particularities thereof should not be considered as being limitative of the scope of the present invention. Unless otherwise indicated, positional descriptions such as "top", "bottom" and the like should be taken in the context of the figures and should not be considered as being limitative.

Figure 4:
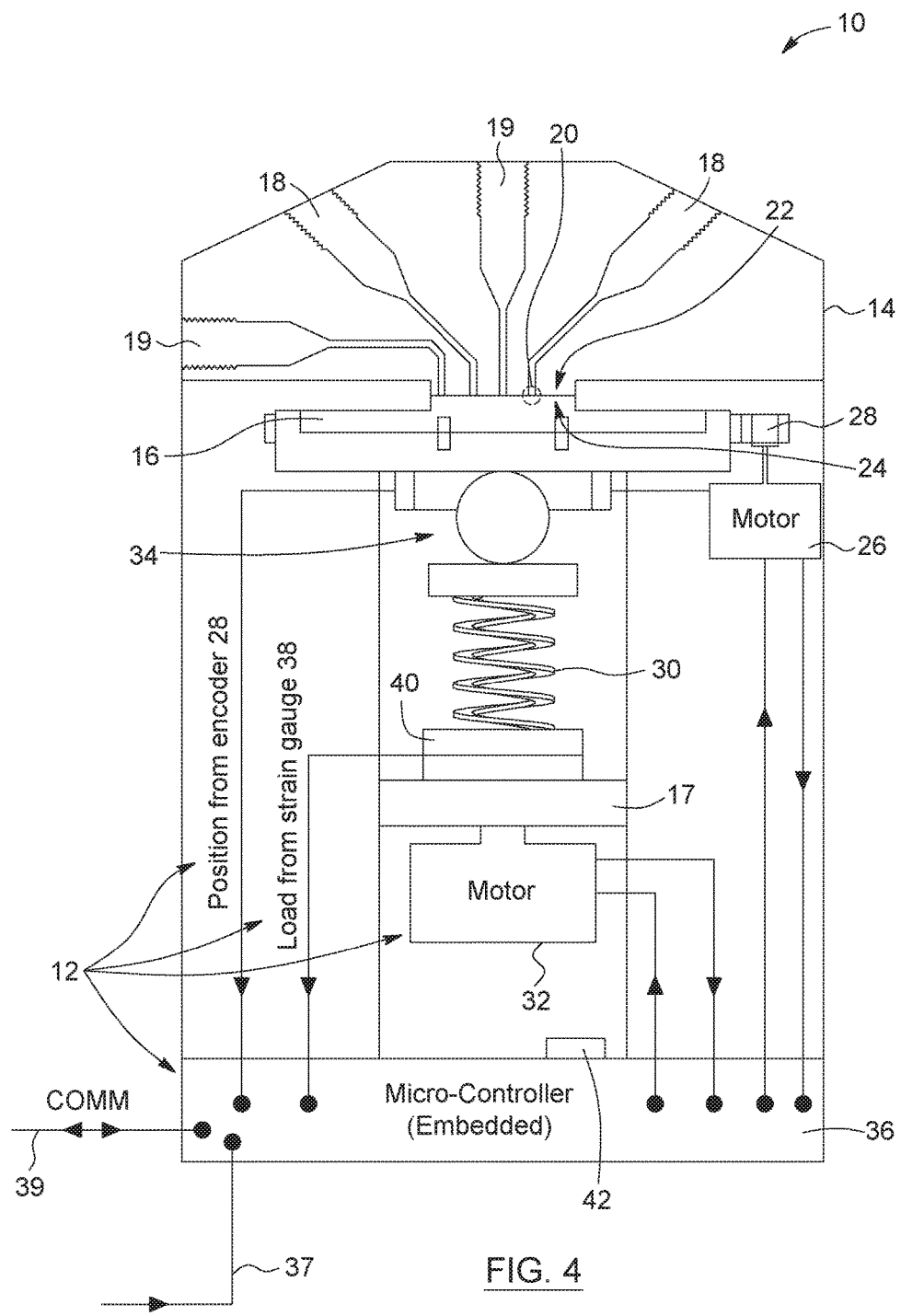
FIG. 4 is a schematic cross-section view of a valve, according to a first implementation of the invention.

With reference to FIG. 4, a first implementation of a valve according to the invention is shown. The valve 10 includes a stationary body 14 provided with fluid passages 18 and 19, for circulating fluid therein at a fluid pressure. The fluid passages can also be referred to as channels. The fluid passages include process fluid passages 18, and also preferably include purge fluid passages 19. The fluid passages 18, 19 open as ports on the body interface 22. The body interface 22 can also be referred to as a sealing surface. For sake of clarity, only one port 20 is identified on FIG. 4, for the fluid passage 18 on the right side of the Figure, but of course each fluid passages 18, 19 opens up as a port on the body interface 22.

In this first implementation, the body 14 is a valve cap, but of course in other implementations, the body 14 can be a valve housing, a ball packing, or an enclosure. The body 14 is a static, stationary part which comprises the fluid passages in which the fluid circulated or is blocked.

The valve 10 also includes a valve element 16, which in the present implementation is a rotor. The valve element 16 is the movable element of the valve 10 which blocks or permits fluid to enter through the different ports of the stationary body 14. In other implementations, the valve element 16 can be the ball of a ball valve or the sliding plate of a sliding valve. In the case of rotary valves, the valve element 16 includes at least one channel though or in which the fluid passes when two ports are connected.

The valve element 16 has a valve element interface 24 which faces the body interface 22. The valve element 16 interacts with the ports of the body interface 22. The valve element 16 moves between different positions so as to permit or obstruct communication between the fluid passages 18 or 19. In the present case, the valve element 16 is a rotor which includes at least one channel, which can consist of grooves for placing ports of the stationary body 14 in fluid communication with one another. The interfaces of stationary body 14 and the valve element 16 can present different types of configurations, an example of which is shown in FIG. 3. In operation, interfaces 22, 24 are in sealing contact and frictionally engaged with each other.

An actuating mechanism 26, which is in this implementation a motor, is used to move the valve element 16 between the different positions. A biasing element 30 is configured to bias the valve element interface 24 against the body interface 22. The biasing element 30 is an element urging the valve element 16 against the stationary body 14. The biasing element 30 applies a sealing load force on the valve element 16, ensuring that a minimal sealing is applied at all time during the valve operation. The minimal sealing load force can vary according to the different applications in which the valve is used.

A load varying mechanism 12 is configured to variably load the biasing element 30 based on the different positions of the valve element. The biasing element 30 thereby applies different sealing load forces on the valve element 16 based on the different positions of the valve element. When the valve 10 is operated, the load varying mechanism 12 configures the biasing element 30 so that it applies a high process sealing load force when ports are in communication or blocked, and a high level of sealing is required. The load varying mechanism also configures the biasing element so that it applies a lower, movement sealing load force when the valve element is moved, and a lower level of sealing is acceptable or desired. Reducing the sealing load pressure, which can also be viewed as releasing the pressure on the valve element, in turn reduced friction between the interfaces 22, 24.

In the present implementation, the biasing element 30 is a spring assembly compressible to different heights, for applying different load sealing forces on the valve element 16. Other types of biasing elements can also be considered, such as tension or compression helicoidal springs, a stack of Belleville washers and the like.

In this implementation, the stator interface 22 is coated with a thick polished layer of TiN (Titanium Nitride), such material being a very hard and inert material. Other material can be considered, such as WC/C (Tungstene Carbide/Carbon), c-BN (cubic Boron Nitride), DLC (Diamond-like carbon) and CrN (Chromium Nitride). However, it was found that reducing the sealing load force on the valve element upon valve actuation also greatly decreases wear of an uncoated stainless steel stator, thereby improving the valve's lifetime. Preferred materials for the rotor are PEEK, Polymide, PPS or a fluoropolymer, such as PTFE. The machined or etched grooves within the valve element 16 are also preferably designed to tolerate high process and mechanical pressures. The actuating system 12 allows can be easily replaced or modified when required. The mechanism 12 also allows for an easy integration within existing analytical systems and can be used as an intelligent subsystem.

The actuating mechanism, which is in this case a motor 26, allows rotating the valve element 16.

The load varying mechanism 12 controllably compresses the biasing element 30, for applying a predetermined sealing load force on the valve element 16. In the present implementation, the load varying mechanism 12 comprises a movable member 17, which can be raised or lowered, for compressing or decompressing the biasing element 30, the movable member 17 being operatively linked to the valve element, in this case via a controller 36.

In the present implementation, the load varying mechanism 12 also includes the motor 32 and the controller 36. The controller receives on a input the different positions of the valve element 16, either by the motor 26 or by a position sensor 28. The controller 36 controls the motor 32 based on the different positions received from motor 26 or sensor 28. Of course, it can be considered to control the motors 26, 32 independently from one another, with separate controllers.

Preferably, a parallelism compensation assembly 34 is used to compensate for any misalignment of the biasing element 30. In the present case, the parallelism compensation assembly 34 includes a bearing ball placed between the biasing element 30 and the valve element 16.

Preferably, the motors 26 and 32 are electrical motors, and the controller is micro-controller 36 embedded in the rotary valve 10. The micro-controller includes a 24 volts DC input 37, as well as one or several communication ports 39. Of course, other operating voltages can be considered. This micro-controller 36 can also be used to control the rotation speed of the valve element 16, via the motor 26.

Preferably, load varying mechanism 12 can be operated with a power supply ranging from 12 to 24 VDC. The built-in micro-controller 36 can be accessed through a simple digital interface. Alternatively, various serial interfaces such as I$^2$C, SPI, CAN, USB, etc. can be supported. It can also be considered to control the motor 32 and/or motor 26 using only a pair of wires, for example by connecting them to another control system or to daisy-chain more than one valve together, on a network, such as an RS-485 system for example.

Using one specific load varying mechanism configuration allows the sealing load force applied on the valve element 16 to be tuned in real time, as the valve operates, with the right force values during rotation and at the end of the maneuver. It can be considered to use the rotary valve 10 in combination with a pressure monitoring system, allowing the valve to be tuned, or controlled, in real time, in order to adjust the sealing loading force applied on the valve element 16 during the movement of the valve element, and optionally based on the process fluid pressure. This way, the lifetime of the valve is increased by avoiding the use of an unnecessary high loading force.

Furthermore, a force transducer 40, based on a strain gauge or some other similar device, can be used to monitor the load on the valve element 16. The force transducer is operatively linked to the controller 36. This monitoring system can also be used to detect an eventual softening of the biasing element 30. In this situation, when the transducer detects a lower load force from the biasing element, the controller 36 increases the compression of the biasing element 30 using the motor 32, for compensating this softening, in order to obtain the required load reading from the strain gauge 40.

Purge outlets of the valve 10 can also be monitored or analyzed periodically in order to assess the condition and integrity of the valve.

It is also possible, via the controller and analytical instrument software, to set the valve 10 in stand-by mode. In this case, the sealing load force is decreased to reduce the stress on the valve element 16. This helps to reduce the possibility of adhesion phenomenon when the valve 10 is not in operation for an extended period of time. Furthermore if, for any reason, the valve stays between two operational positions for a long period of time, the lower rotation load force will greatly decrease the possibility for the rotor material to extrude into the ports of the stationary body 14. Extrusion of the rotor material into the process ports can be a problem with softer rotor material like Teflon.

In some gas chromatography applications, such as complex hydrocarbon analysis, the required operating temperature can be as high as 350° C. In this case, it is advisable to add a small temperature sensor 42 in the valve, such as a miniature RTD or a thermocouple. The sensor 42 sends information signals to the controller 36, which in turn will control the motor to vary the sealing load force applied on the rotor, based on the temperature readings of the sensor 42. The sensor 42 can thus help compensating for the softening the biasing element 30 or the different thermal expansion of each of the many parts of the valve 10. In other words, the temperature sensor 42 detects operating temperatures of the valve 10 and to send the temperatures detected to the controller 36. The controller controls analyses the temperature detects and determines whether the motor 32 need to vary the height, or compression, of the biasing element 30. The biasing element is thus variably loaded by the varying mechanism according to the operating temperatures detected by the temperature sensor 42.

In some other applications, the operating temperatures of the analytical systems, and therefore of the valves, must be changed frequently. Polymer hardness may vary greatly depending on the temperature of its application, thereby affecting its ability to seal against the stator. It is advisable to apply different sealing load force schemes according to each of those system temperatures. Furthermore, due to creep phenomenon, applying the same load on a polymer valve element 16 at high temperature rather than at ambient temperature could permanently deform and damage it. The controller allows avoiding damaging the valve element 16, by controlling the motors 26, 32 in function of various operating factors, such as operating temperatures, fluid pressure, type of fluid being analysed.

In this implementation, the valve 10 includes the position sensor, or detector, 28 which allows determining the angular position of the valve element 16, also referred to as a rotor relative to the stationary body 14, also referred to as a stator for this type of valve. For example, a digital encoder may be used as the position sensor 28. The detector 28 can also be used to indicate and control the position of the valve element in a sample stream selection valve. The position sensor 28 is preferably part of the load varying mechanism 12, and is connected to the controller 36. It detects the different positions of the valve element 16 and sends the detected positions to the controller 36, which can adjust, via the motor 32, the load force applied on the valve element 30 as a function of the different positions of the valve element 16.

Still preferably, the actuating system 12 includes the force transducer 40, which is also referred to as a load force detector 40. In the illustrated implementation, the detector 40 is a strain gauge, which allows determining the load applied on the valve element 16 by the biasing element 30. Of course, other types of pressure and/or load force detector can be used. The load force can also be deducted or calculated from the power required by motor 32, instead of using an independent load detector.

Still referring to FIG. 4, and also to FIG. 5A, a method of operating the valve according to one implementation will be explained. While the example provided is for a rotary valve, the present method can also be applied to other types of valves, such as sliding valves or ball valves.

At time T=0, the valve element 16 is in a first operating position, which means that at least two process ports of the body 14 are in fluid communication. A sealing load force A, which can also be referred to as a process sealing load force, is applied by the biasing element 30, pushing the valve element, in this case the rotor 16, on the body 14, so that the valve element and the body interfaces 22, 24, or sealing surfaces, are sealed to one another. To do so, motor 32 compresses the biasing element 30, so that it applies the load force A on the rotor 16, which corresponds to the sealing load force. During this period $T_S$ (from T0 to T1), the rotor is stationary, and fluid(s) can be circulated through channels and grooves of the stator 14 and rotor 16, respectively.

At time T1, prior to rotating the rotor 16, the motor 32 lowers the plate supporting the biasing element 30, thereby decompressing the biasing element 30. The load force applied by the rotor 16 on the stator 14 is now reduced to the rotation startup load force, indicated as "D" on the graph of FIG. 5A. It is known that when applying a substantial sealing force on the rotor, the load applied is so great that the rotor 16 tends to adhere to the stator 14. Consequently, in order to start rotating the rotor, it is needed to overcome the frictional forces created by this adherence, and thus a relatively high torque needs to be applied by the actuator, in this case the motor 26. Lowering the pressure at time T1 below the static friction, and preferably to 0, allows releasing the rotor 16 from the stator 14 prior to rotating the rotor 16, which in turn diminishes the required torque at the rotation start-up. The rotation start-up load can be applied for a very short period of time $T_{R\ start-up}$, for example between 50 ms and 100 ms. The rotation start-up load (D) is determined depending on the type of process application for which the valve is used. For example, the rotation start-up load is determined depending on whether small leaks in the valve are acceptable or not. Of course, it can be considered to provide the rotor with process purging grooves, as disclosed in U.S. Pat. No. 7,503,203.

Between T1 and T2, the motor 1 slightly raises the plate supporting the biasing element 30 until load force C is detected by the strain gauge 38. The load force C corresponds to the rotation sealing load force.

It is possible to start the rotation of the rotor at time T1, but it is can be considered to wait until T2. As such, when the rotation sealing load force C is reached, motor 26 rotates rotor 16 from a first to a second operating position, so as to place different process ports in fluid communication. The period extending between either T1 or T2 and T5 thus corresponds to the period $T_R$, during which the rotor 16 is rotated. Optionally, an intermediate load B can be applied, between T3 and T4. This intermediate load force can be applied for example when purging the valve channels or when crossing over ports.

Figure 5B:
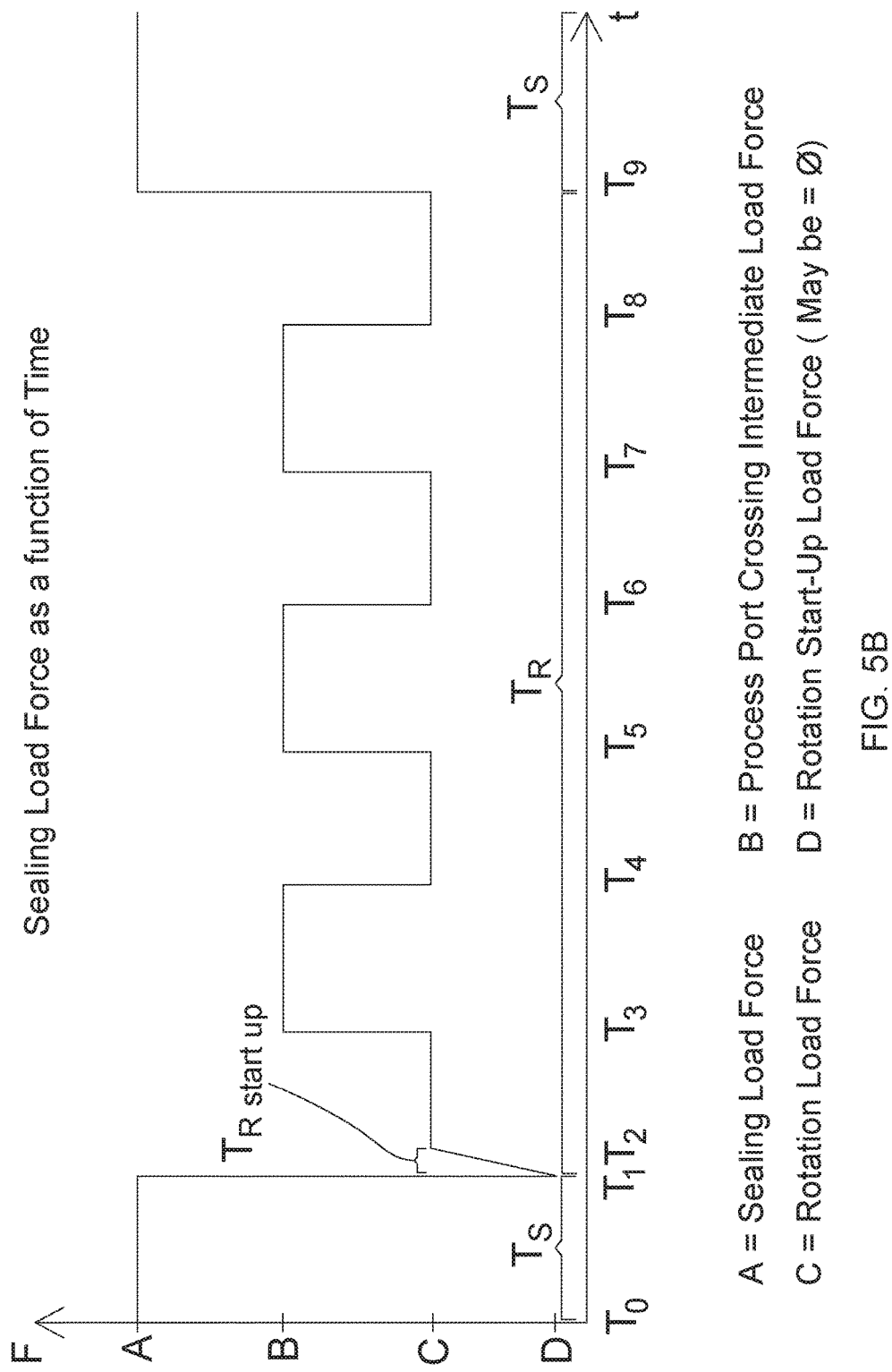
FIG. 5B is a graph of the load force applied on the valve element of FIG. 4, as a function of time, according to another implementation of the method.

Referring to FIG. 5B, in one implementation the load force is increased to the intermediate sealing load force B during three periods, each period corresponding to the rotor crossing over an intermediate port. Increasing the loading force to an intermediate loading force allows limiting the leaks and/or contamination risks when crossing over a port, since the sealing of the valve is increasing during this period. The intermediate loading force does not need to be as high as the sealing load force, and can be chosen to correspond to an acceptable leak rate, depending on the type of application in which the valve is used.

Turning back to FIG. 5A, at T5, the rotor is placed in the second operating position and the load force is increased to the sealing load force A. In the present case, and in reference to FIG. 4, the sealing load force is increased by raising the plate supporting the resilient element so as to compress it. The motor 32 raises the movable member 17 until the strain gauge detects that load force A has been reached.

Figure 11:
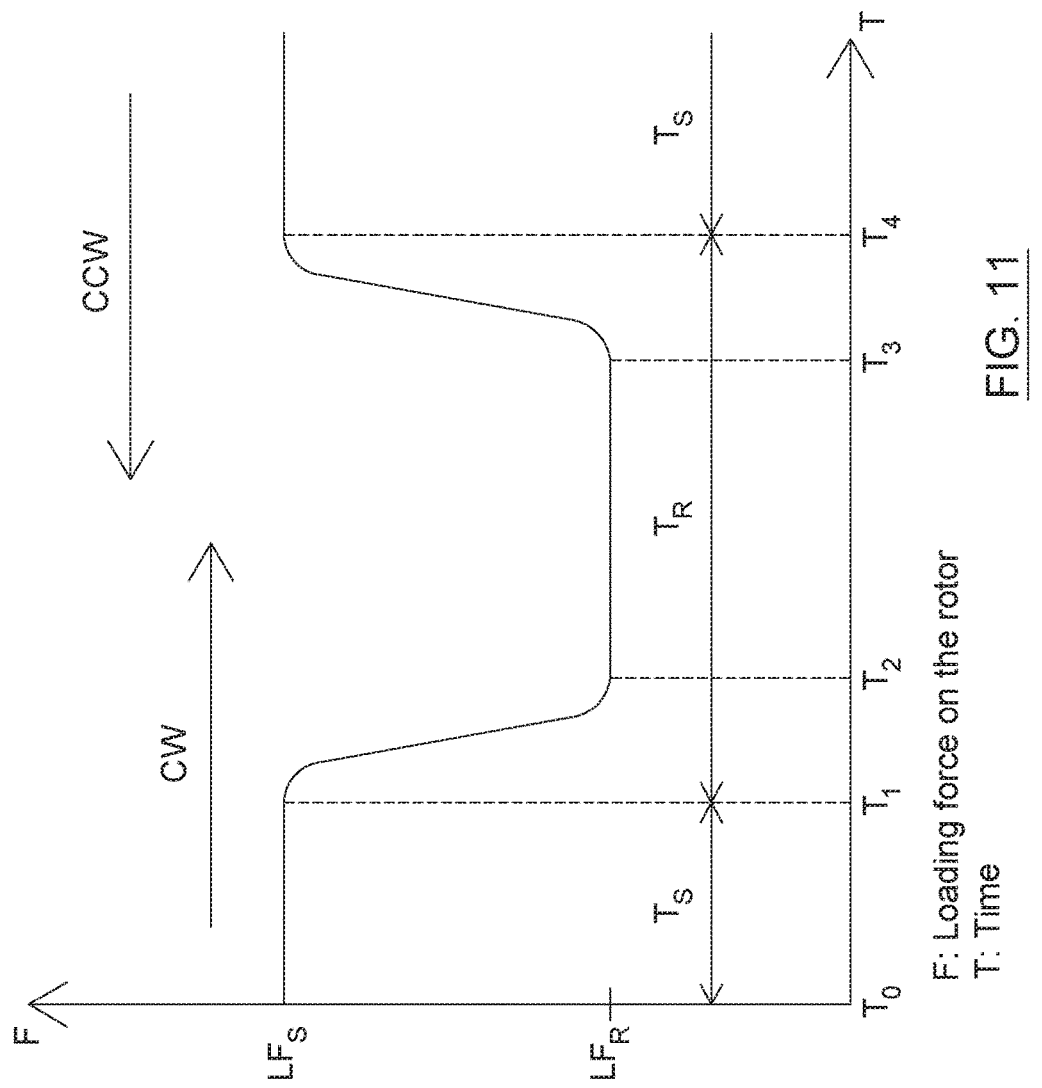
FIG. 11 is a graph of the sealing load force applied on the rotor of the valve of FIG. 6, as a function of time.

Of course, in order to increase the operating time life of the valve, it is possible to gradually increase and reduce the sealing load force applied on the rotor while rotating the rotor, such as shown in the graph of FIG. 11. Alternatively, the sealing load force can be first reduced to the rotation load force, prior rotating the rotor.

Preferably, operation of motor 26 and 32 is controlled based on readings from the position detector 28 and the load detector 38. The controller receives position and load force (or pressure) signals from their respective detectors and sends instruction signals to motors 26, 32 accordingly.

As can be appreciated, the method described above includes as step of applying a sealing load force when the valve element is stationary and the valve is in operation, and of applying a reduced sealing load force, while moving the valve between the different positions. In other words, the sealing load force is applied at a process sealing load force when two or more ports are blocked or in communication, and the valve element is stationary. Slightly prior to, or upon moving the valve element, the sealing load force is reduced to a movement load force, so as to reduce friction and wear at the valve element and body interfaces. The sealing loading force applied on the valve element 16 is less, or smaller, when the valve element is moved between two positions, than when the valve is in operation and stationary. When the valve element reaches, or is about to reach one of its operating positions, the loading force applied on the valve element is increased until the sealing load force is reached, in order to properly seal the valve element to the housing or stator, during operation of the valve. The movement load force ensures a minimal sealing between the valve element and the housing, corresponding to a tolerable leak rate, which may vary according to the application for which the valve is used. Optionally, the sealing load force is generated irrespectively of the fluid pressure. The decrease of the sealing load force can occur rapidly, such as when using a motor as shown in the implementation of FIG. 4, and in graphs of FIGS. 5A and 5B, or it can be performed gradually as the rotor moves between the different positions, as is the case with the second to the fifth implementations explained later on.

When the valve element begins moving between two positions, and preferably slightly before the movement start-up, the loading force is reduced to a smaller loading force until it reaches a predetermined "movement loading force". The movement loading force can be kept relatively constant or be varied until the next desired operating position is reached. The load force and pressure is thus released during movement of the valve element, thereby reducing friction between the housing and the valve element, and the load force and pressure is re-applied when the valve element is in the next operating position, to ensure proper sealing.

According to the present method, when the valve element is moved, the loading force pressing the valve element 16 against the body 14 may be reduced well below the level that is normally required to seal the valve 10 at the operating process pressure. It may be reduced enough to maintain the sealing integrity, or reduced below the point where a tolerable leak occurs, in which case the purge groove can palliate for such leak. The valve is then quickly moved. The friction is therefore much lower, as is the wearing and the particle generation.

When in an operating position, the loading force pressing the valve element 16 against the body 14 can be increased well over the loading force generally used in standard valves, without risking of wearing the sealing surfaces or polymer extrusion through ports.

Reducing the sealing load force during movement of the valve element 16 between operational positions allows avoiding that portions of its sealing interface (ie the surface of the rotor contacting the stationary body 14) be sliced by an extrusion effect into the ports of the body 14. Indeed, when softer material are used for the construction of the rotor and/or rotor interface, and when the sealing load force in maintained constant during rotation of the rotor, extrusion of the sealing surface of the rotor can occur within the ports of the stationary body, which generates particles and increases wear of the rotor. Softer materials, which typically have a D shore of less than 75, have good sealing properties, but this advantage becomes a disadvantage if the load force is maintained constant when the valve element 16 slides or rotates against the body 14 between positions. The reduction of the sealing load force during movement of the valve element against the stationary body allows using softer materials for the rotor that could not otherwise be considered. Examples of softer materials include perfluoroelastomers, such as Kalrez® with a hardness/D shore value of 25, PFTE (Polytetrafluoroethylene, such as Teflon®), with a D shore value of 65. Of course, harder materials can also be used for the valve element of the present valve and method, such as PEEK (Polyether Ether Ketone) and VESPEL® with a D shore of 85 and PPS (Polyphenylene Sulfide) with a D shore of 90.

Referring to FIG. 5C, it can be considered to vary the load applied on the rotor according to the process pressure, and based on the type of material of which the rotor is made. The process pressure corresponds to the pressure of the fluid circulating within the valve. For lower pressure applications, the load applied on the rotor can be less, and sealing of the rotor against the stationary body is still sufficient. For higher pressure applications, higher loads must be applied on the rotor to seal it properly against the stationary body. As shown in the graph, the load (and consequently the sealing load force) is reduced during rotation of the rotor, compared to when it is stationary (indicated as "sealing load"). Also, Material B being softer than material A, the sealing load applied on the rotor is less than for a rotor made of Material A.

Increasing the rotor loading force when the valve is at its final (or operational) position, combined with a selection of proper materials, leads to an increased sealing efficiency when a relatively high pressure is used, without being plagued with the premature wear generally associated with valve operated with high sealing force load. Furthermore, for the purpose of cleaning surfaces of the valve, a cleaning intermediate force can be applied to allow a solvent or other appropriate cleaning/washing fluid to flow on all surface area without having to dismantle or disassemble the valve. This cleaning intermediate load is lower than the rotation load. Depending on the type of application in which the valve is used, that load can be low enough to allow the rotor to be slightly spaced from the stator.

Preferably, the method includes a step of compressing the biasing element to a first height when two ports of the housing are in fluid communication and the valve element is stationary in a first position; and a step of decompressing the biasing element up to a second height, thereby reducing the sealing load force applied on the valve element as the valve element moves towards a second position so as to interrupt flow of the fluid between said two ports.

Preferably, the method includes a step of recompressing the biasing element to the first height, when said two ports or other ports of the housing are in fluid communication and the rotor is stationary in the second position. It can also be considered to recompress the biasing element to the first height, when said two ports of the housing are blocked by the valve element and the rotor is stationary in the second position.

Now referring to FIGS. 6 to 11, another implementation of a valve is provided. In this implementation, the valve is a rotary valve 100 having a body 140 provided with a cavity 142 bordered by a sidewall 144 (identified in FIG. 8). The sidewall 144 includes the body interface 220. In this implementation, the valve element is a rotor 160 disposed within the cavity 142. The rotor 160 has at least one channel 190, 191 opening on the interface 240 for interacting with the ports 200 of body interface 220. The rotor 160 is rotatable between different process positions, which are in this case angular positions, so as to permit or obstruct communication between the fluid passages 180 via the at least one channel 190. The actuating mechanism includes a rotatable shaft 126 connected to the rotor 160. The biasing element 130 is a compression spring assembly 130, and more particularly a stack of Belleville washers.

The load varying mechanism 120 includes a static member 122, fixed in place thanks to a stopper 125, and the movable member 121. The movable member 121 comprises a portion 129 (identified in FIG. 8) operatively linked to the rotor 160 so as to rotate along with the rotor, and a face 131 slidably in contact the face 132 of the static member 122 (the faces are identified in FIG. 7). The faces 132, 131 of the static and movable members 122, 121 have respective profiles configured to move away or bring closer the static and movable members 122, 121 as the rotor rotates, thereby compressing or decompressing the biasing element 130. In other words, the static member and the movable member form an assembly having an overall height which can vary according to the position of the movable member 121. Since the members 121, 122 and the biasing element 30 are are contained within the body 140 of the valve, varying the height of the member assembly necessarily varies the height, and thus compressibility of the biasing element 130, which in turn affect the sealing load force applied by the biasing element on the rotor 160.

The rotary valve illustrated in FIGS. 6 to 10 is a conical rotary valve 100. The body 140 is a housing having top and bottom ends. The rotor 160 has a frustro-conical body with a narrow end and a wide end. The rotor 160 fits within the cavity 142 with its narrow end disposed at the top end of the body 140. The at least one channel consisting in at least one groove 190 disposed at the surface of the frustro-conical body. The rotatable shaft 126 is connected to the narrow end of the frustro-conical body 160 and extends outwardly of the housing 140 top end.

The load varying mechanism 120 is disposed at the wider end of the frustro-conical body; and the spring assembly 130 is disposed beneath the load varying mechanism 120. The conical rotary valve 100 includes a disk 126 fixed at the bottom end of the housing, ensuring that the the spring assembly 130 is compressed with a minimal sealing load force. The disk 126 also closes off the cavity 142. Of course, the disposition of the load varying mechanism 120 and the biasing element 130 can be inverted, and the mechanism 120 and element 130 could be placed above the rotor 160 instead. Many possible configurations can be considered.

Figure 9:
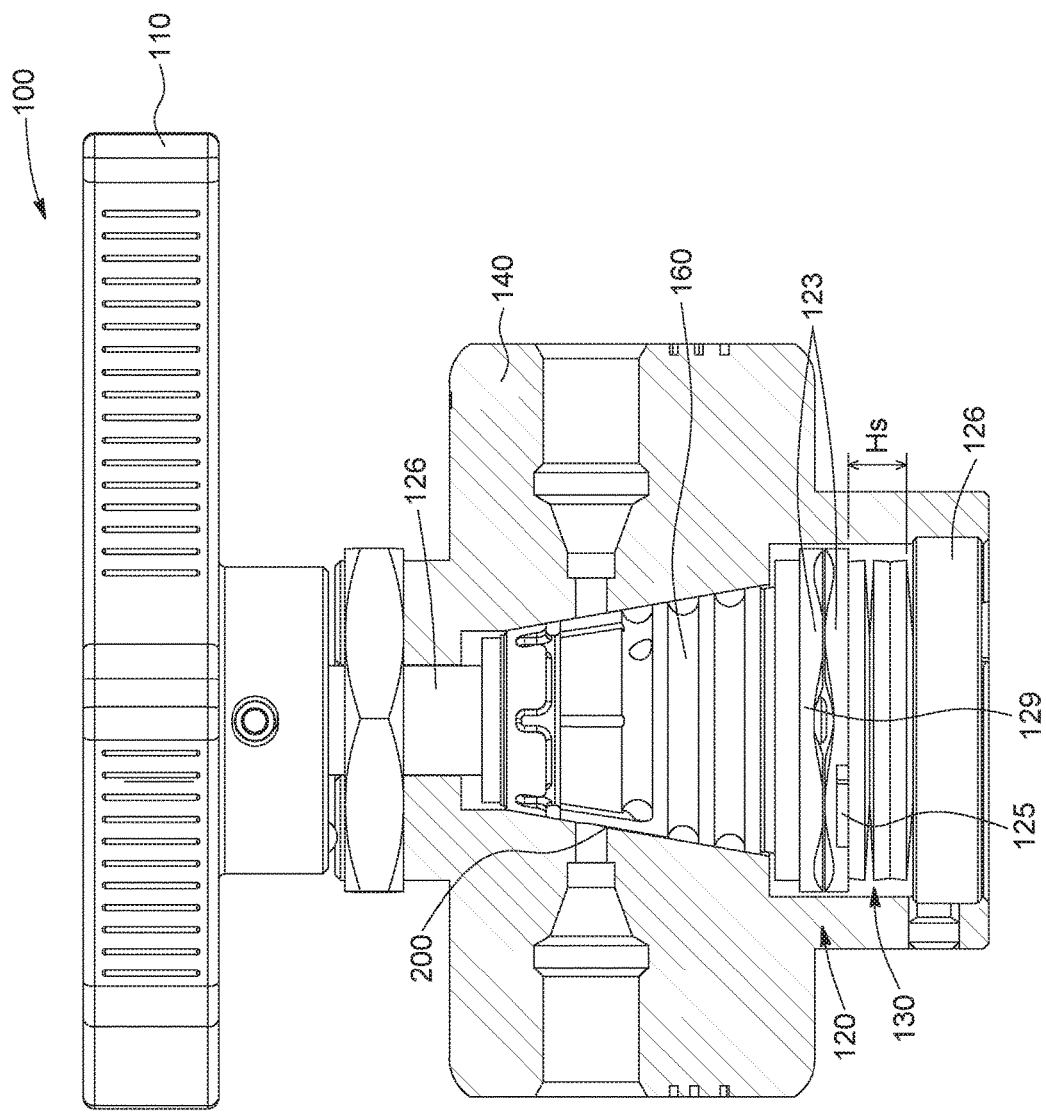
FIG. 9 is a side view of the rotary valve of FIG. 6, with the housing shown in cross-section, in a configuration where two ports are in fluid communication and the rotor is stationary.

In this implementation, the static and movable members of the load varying mechanism 120 are first and second cam washers 122, 121, their respective faces 131, 132 including concave and convex portions 129, 123 (identified in FIGS. 9 and 10). in a first configuration, as shown in FIG. 9, the respective convex portions 123 of the cam washers 121, 122 are in contact, thereby compressing the compression spring to a height Hs. In a second configuration, the respective convex and concave portions 123, 127 are mated, thereby decompressing the spring assembly 130 to a height Hr, Hr being greater than Hs, thereby reducing the load force applied on the rotor 160.

Figure 7:
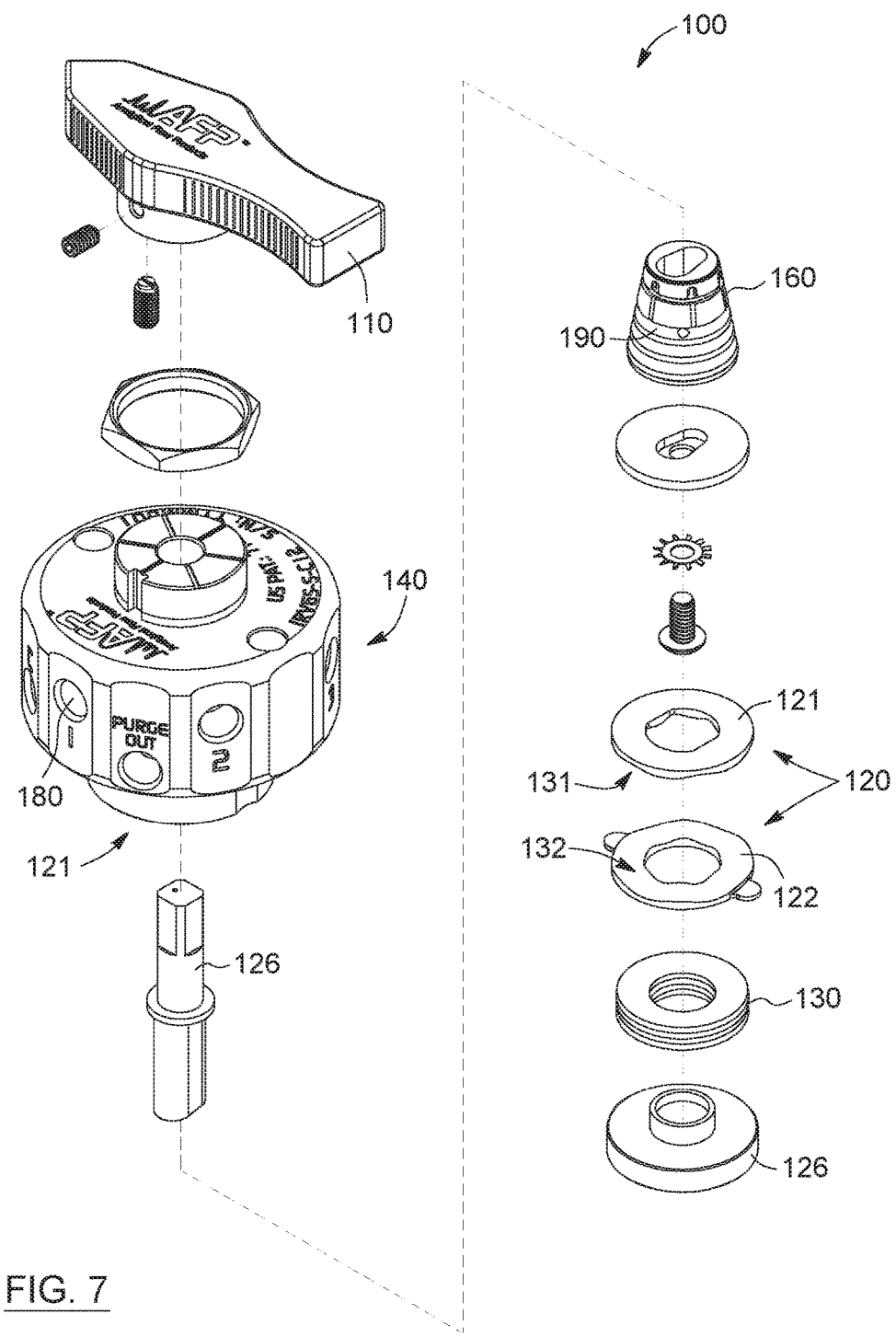
FIG. 7 is an exploded view of the rotary valve of FIG. 6.

FIGS. 6 and 7 show the conical rotary valve 100. The valve 100 includes a stator 140. The stator 140 is provided with several channels, or fluid passages, 180, 181 through which process or purge fluids can be injected or drawn. A handle 110 allows moving the rotor housed in the stator 140 between different operating positions.

Figure 8:
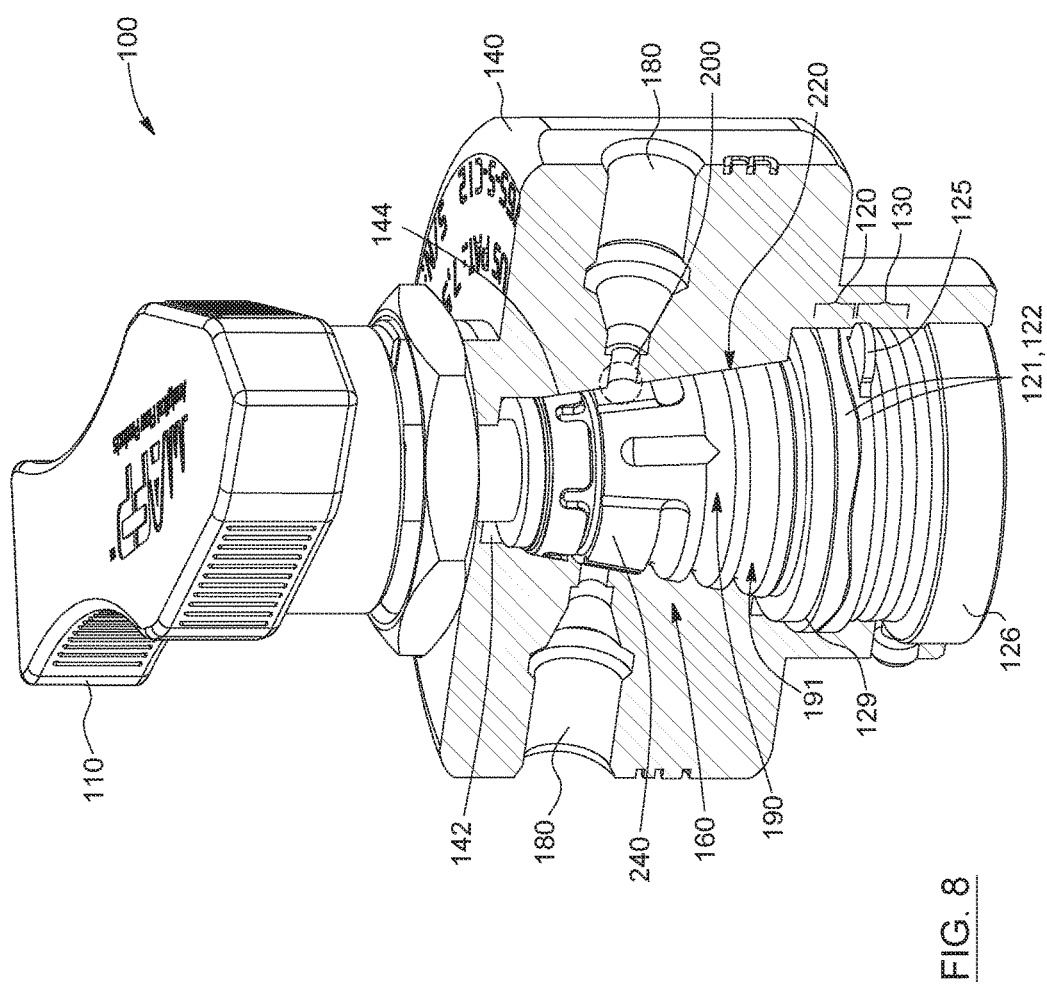
FIG. 8 is a perspective view of the rotary valve of FIG. 6, with the housing shown in cross-section.

Still referring to FIG. 8, the conical rotary valve 100 is provided with the stator 140 shown in cross-section. The valve includes ports 200 opening on the stator interface 220 and grooves 190, 191 provided on the rotor sealing interface 240. The grooves 190 allow placing selected process ports (one port 200 is identified on FIG. 8) of the stator in fluid communication with one another, depending on the position of the rotor 160. Biasing elements 130, which are located below the rotor 160, allow pressing the rotor 160 against the stator 140 so as to seal the sealing surfaces of the rotor and stator when the valve is in operation. In the present case, the biasing element 130 is a stack of Belleville washers. The rotary valve 100 also comprises load varying mechanism 120, which in the present case consists of two cam-washers 121, 122. The Belleville washers are compressed between the mechanism 120, and a disc 126, which is fixed within the stator 140.

Now referring to FIG. 9, the rotary valve 100 is shown in a first operating position, two process ports of the stator being in fluid communication, port 200 and a common outlet port not shown. The cam washers 121, 122 are positioned such that their respective convex portions 123 are in contact, compressing the biasing element 130 such that its overall height corresponds to a height H. In this position, the biasing element 130 applies a sealing loading force LFs on the rotor. Upon turning the handle 110, the upper cam-washer moves along with the rotor 160, while the lower cam-washer will stay fixed, thanks to a stopper 125, which is best shown in FIG. 7. The respective surfaces of the cam-washers slide one on the other, gradually increasing the height H of the resilient element 130 until the configuration shown in FIG. 9 is reached.

Figure 10:
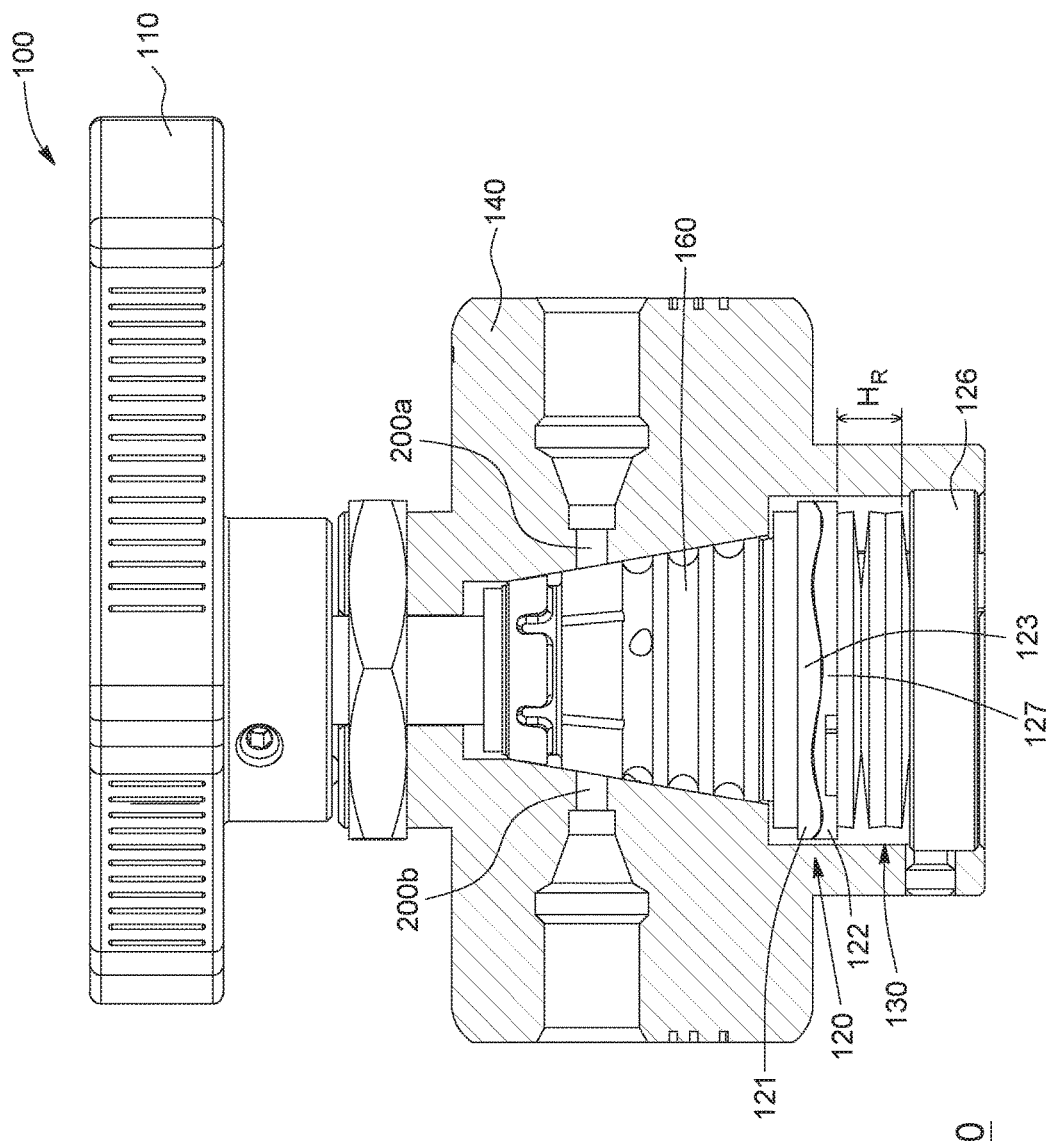
FIG. 10 is a side view of the rotary valve of FIG. 6, with the housing shown in cross-section, in a configuration where fluid communication is prevented between two ports, the rotor being rotated.

As shown by FIG. 10, the rotor 160 is now positioned so that the process ports of the stator 140 are no longer in fluid communication. The rotor is now located at mid-point between two operating positions. Convex and concave portions 123, 127 of the respective cam-washers are aligned and the cam washers are mated with one another. The overall height of the biasing element is increased to $H_R$, $H_R$ being larger than H. As such, the static biasing element 130 is now slightly decompressed, which reduces the load force applied on the rotor 160.

As explained above, the resilient biasing element 130 is located between the cam washers 121, 122 and the fixed plate 126, which is preferably screwed to the stator 140. The lower section of the biasing element 130 rests on this fixed plate 126. As such, rotating the handle, and thus of the upper cam washer 121 results in compressing or decompressing the biasing element 130, and thus in releasing or increasing the pressure applied on the rotor 160. Advantageously, when the rotor is moved from a first to a second operating position, the pressure is gradually reduced and then increased again until the second operating position it reached.

FIG. 11 is a graph presenting the loading force applied on the rotor in function of time. Between times T0 and T1, a sealing load force $LF_S$ is applied on the rotor, which corresponds to the valve position shown in FIG. 9, namely a first operating position. This sealing load force is applied during a period Ts, during which the valve is operated. Between times T1 and T2, the rotor is rotated and the pressure applied on it is gradually reduced until it reaches a relatively constant rotation load force $LF_R$. The period between T2 and T3 corresponds to the valve position shown in FIG. 10. At time T3, the rotor is rotated up to the next operating position, namely the second operating position, which is reached at time T4. At this time, when the rotor is stopped, the actuating system has increased the loading force back to LFs. In order to move the valve back to its original position, the actuation process can be repeated in the opposite direction.

Referring now of FIGS. 12 to 25, three other implementations of the valve according to the invention are shown. The different variants of the valve are rotary valves, and more specifically they are ball-valves, 1000, 1000' and 1000".

Figure 12:
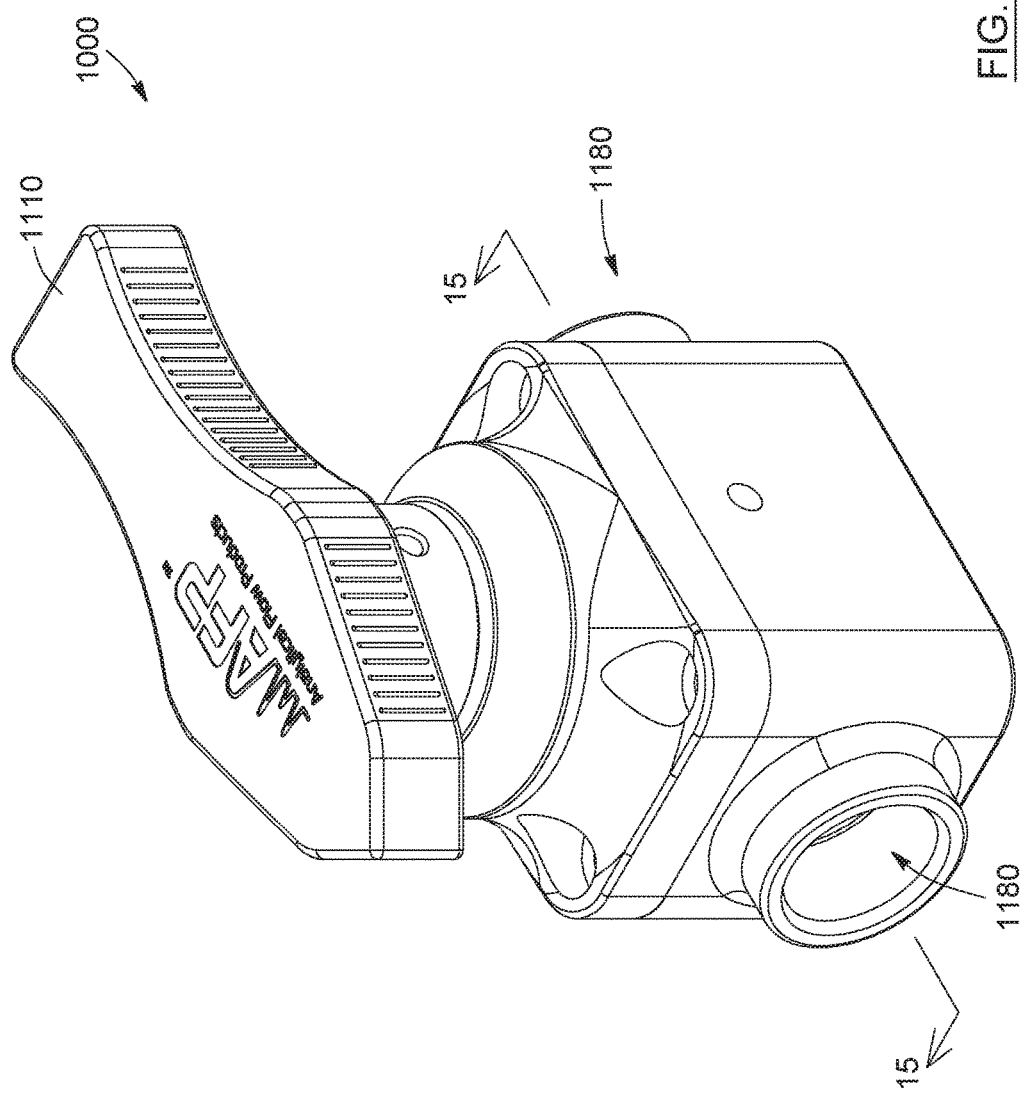
FIG. 12 is a perspective view of a ball valve, according to a third implementation of the invention.

Referring to FIG. 12, the first variant of a rotary ball-valve 1000 is shown. The valve 1000 has a handle 1110 for positioning the valve element, which is in this case a ball, in different positions. In this case, the ball-valve 1000 is a two-way valve, but of course other types of ball-valve can be considered for the valve of the present invention, such as three way L or T valves, shown in FIGS. 25A and 25B. The valve 1000 has fluid passages 1180 for circulating or blocking fluid with the valve 1000.

Figure 13:
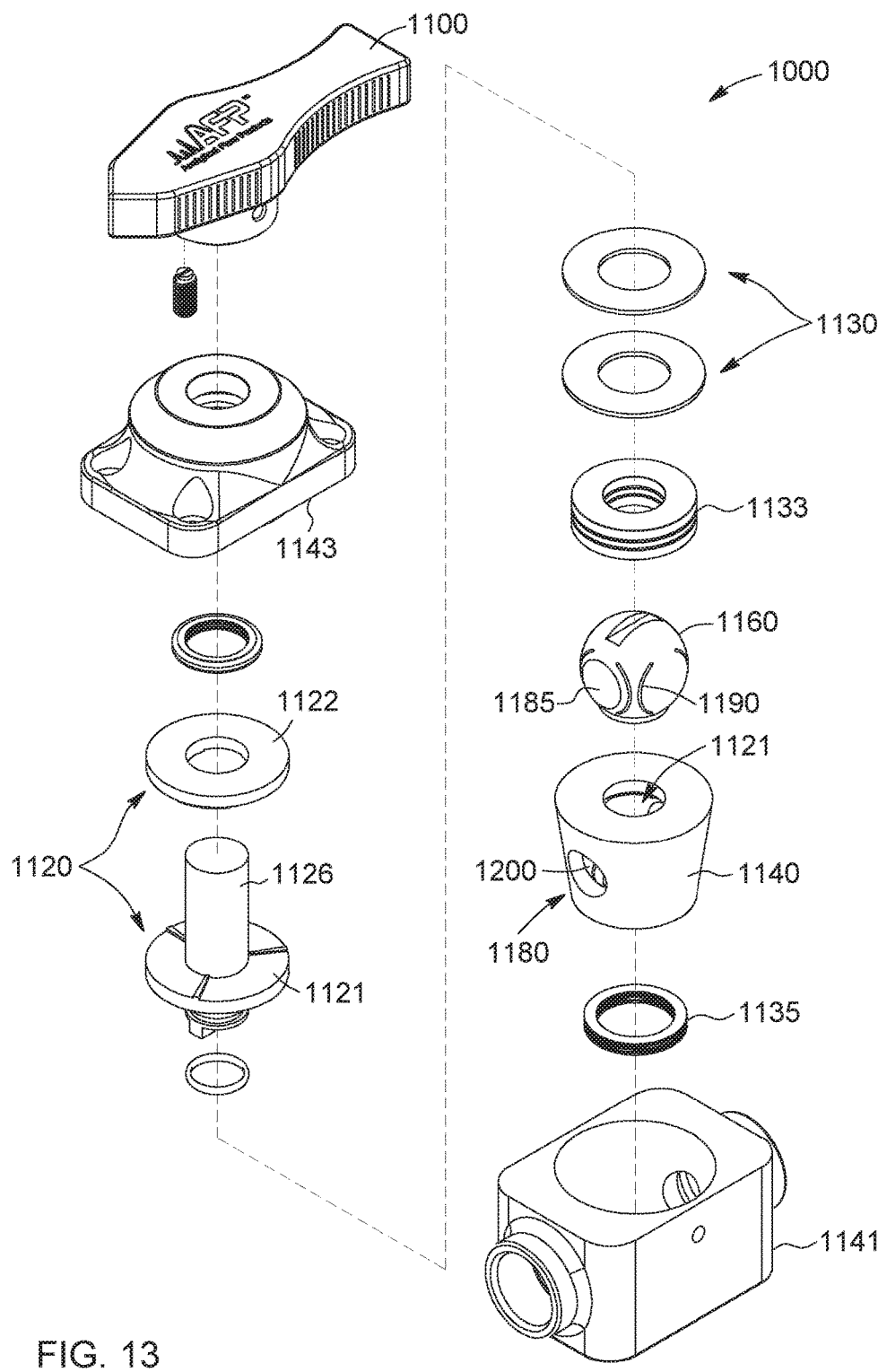
FIG. 13 is an exploded view of the ball valve of FIG. 12.

FIG. 13 is an exploded view of the valve of FIG. 12. The valve 1000 includes the handle 1110, a valve cap 1143, a load varying mechanism 1120, which comprises a movable member 1121 and a static member 1122. The biasing element consists in two Belleville washers 1130. A ball bearing mechanism 1133 is also provided. The valve element is in this case a ball valve 1160, which includes a through channel 1185. The ball is provided with purging grooves 1190, to circulate purging fluid therein. The body, or stator, is a packing 1140 provided with a cavity 1121 for receiving the ball 1160. The packing 1140 has fluid passages opening as ports 1200 on the inner side of the packing 1140. Inside the packing 1140 is the body (or packing) interface 1220 which is in contact with the valve element interface, corresponding in this case to the ball 1160 outer surface. A stack of biasing springs 1135 is provided below the packing 1140, to urge the packing 1140 in place within the valve enclosure, which includes a casing 1141 and a valve cap 1143. The spring constant of the biasing springs 1135 is of course smaller than the one of the resilient element 1130. The biasing springs 1135 are used to prevent the ball 1160 from adhering to the bottom of the packing 1140 when the sealing load force is reduced from the operational, sealing force to the rotational sealing load force.

As can be appreciated, as shown in FIGS. 13, 15 and 16, in this implementation, the rotor is the ball 1160 fitting within the cavity 1121, and the at least one channel is a through hole 1185 extending within the ball 1160. The valve enclosure has top and bottom sides and it houses the packing 1140 and the ball 1160.

The rotatable shaft 1126 has its lower end connected to the ball and an upper end extending outside of the packing 1140 and the enclosure 1141,1143. The load varying mechanism 1120 and the spring assembly 1130 are is disposed above the packing, within the enclosure. In this implementation, a ball bearing 1133 is disposed between the packing 1140 and the compression spring assembly 1130.

Figure 14B:
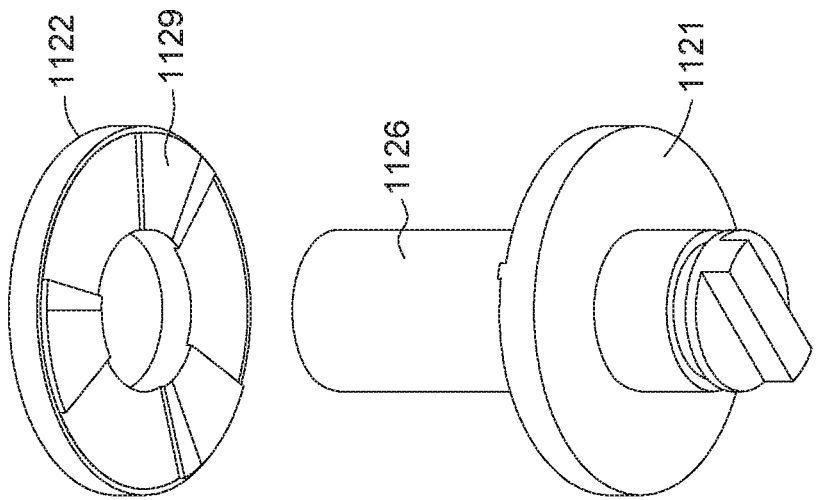
Figure 14A:
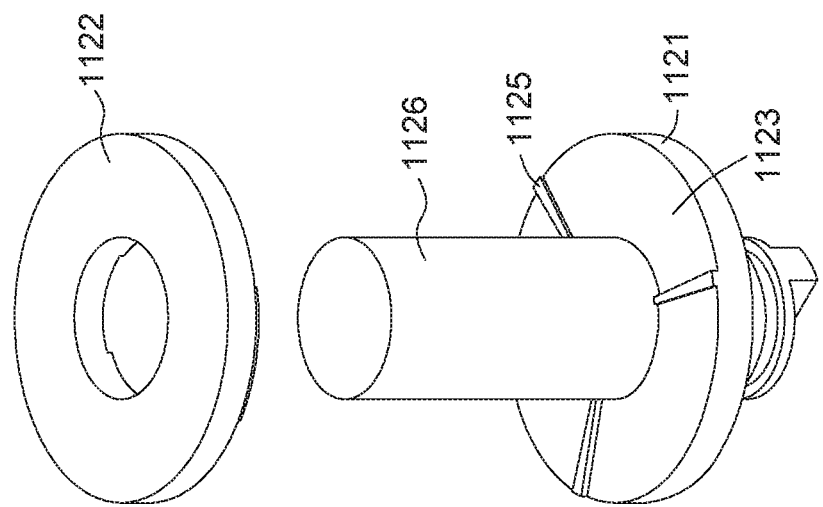

Referring now to FIGS. 14A to 14D, the load varying mechanism 1120 includes static and movable members which in this example are shaped as circular plates 1122, 1121 disposed radially within the enclosure 1141 when in use. The static and fixed members 1121 and 1122 are designed to cooperate when placed in the valve, each members having faces contacting one another, as best shown in FIGS. 15 and 16. In this implementation, the circular plate 1121 of the movable member extends radially from the rotatable shaft 1126, but other configurations can be considered, as long as the movable member is operatively linked to the rotor, so as to move or rotate along the rotor's movement. The plate 1121 has a face with at least one portion with a sloped profile 1123. The sloped profile 1123 is very gentle, as can be seen in FIG. 14D. The face of the static plate 1122 has one sliding block 1129 configured to slide along the sloped profile 1123.

Preferably, the circular plate 1121 includes at least two stoppers 1125 which delimits the portion with the sloped profile. The stoppers also limit movement of the sliding block between the stoppers, and consequently of the ball within the packing. Of course, the sloped profile could be provided on the fixed member 1122, and the sliding block on the movable member 1121. In the present case, the plate 1121 comprises three portions with sloped profile.

Referring now to FIGS. 15, 15A, 16 and 16A, operation of the load varying mechanism 1120 will be explained. The plates 1121 and 1121 are coupled to one another and disposed above the biasing element 1130. The biasing element and the plates 1121, 1122 are contained within the valve cap 1143 and the ball bearing 1133. The total height $H_{TOT}$ is thus fixed and cannot be varied. When the sliding block 1129 is at the bottom of the sloped profile 1123, as shown in FIG. 15A, the overall height of the load varying mechanism is $H_{VL1}$ and the biasing element 1130 as a height $H_{B1}$. When the handle 1100 is rotated, the shaft 1126, plate 1121 and ball 1160 rotate, and the sliding block 1129 slide upwardly along the profile 1123, which increases the distance between the two plates 1121 and 1121, so that the overall height of the load varying mechanism is $H_{LV2}$, thus decreasing the height of the biasing element to $H_{B2}$, $H_{B2}$ being smaller than $H_{B1}$. The biasing element is thus more compressed and exerts a higher sealing load on the ball 1160. In other words, rotating the shaft 1126 forces the sliding block 1129 to slide along the sloped profile 1123, which increases the distance between the static and movable plates 1122, 1121, thereby reducing the height or size of the compression spring assembly 1130.

Preferably, as best shown in FIG. 14D, the portion of the annular plate 1121 with the sloped profile includes two flat portions 1124 disposed on each side of the sloped profile 1123, between the two stoppers 1125. Referring now to the graph of FIG. 24, the profile of the load force applied by the biasing element 130 corresponds to the slope of the surface of the annular plate 1121. By varying the profile of the static and/or movable members of the load varying mechanism, the load force applied on the valve element can be modulated accordingly.

Figure 18:
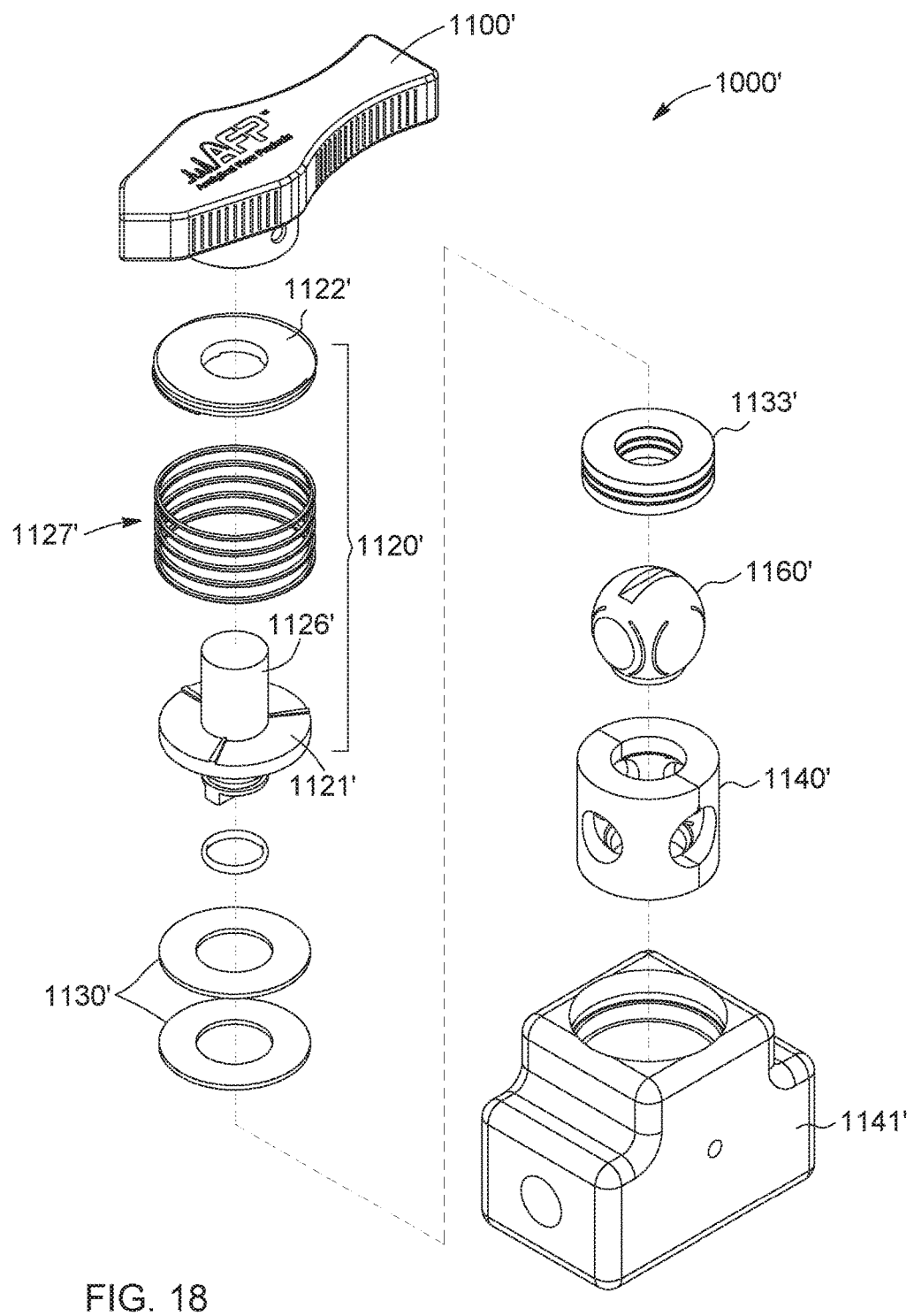
FIG. 18 is an exploded view of the rotary valve of FIG. 17.
Figure 19C:
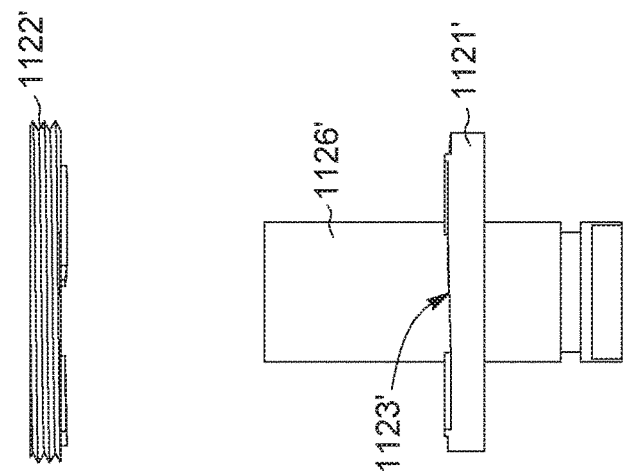
FIGS. 19A, 19B and 19C are a top perspective view, a bottom perspective view and a side view, respectively, of two components of the rotary valve of FIG. 17.
Figure 19B:
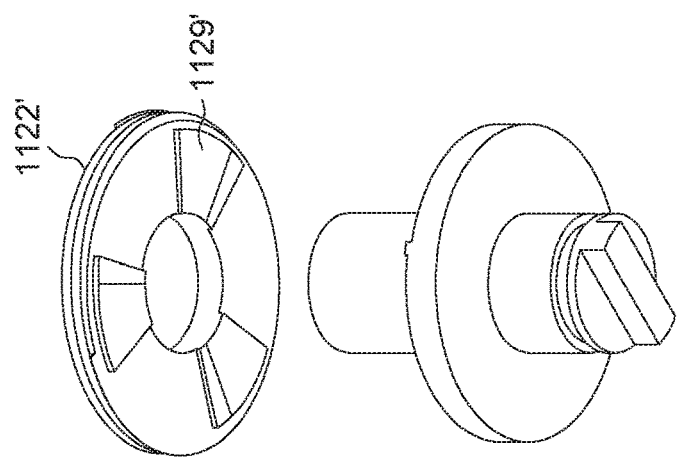
Figure 19A:
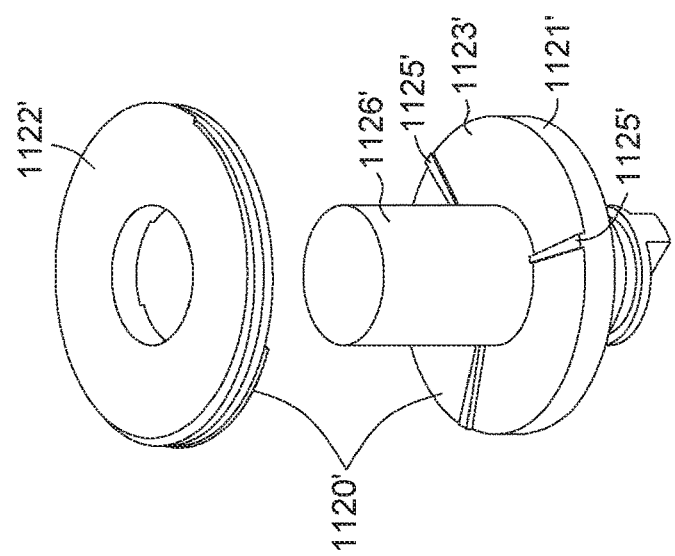
Figure 20:
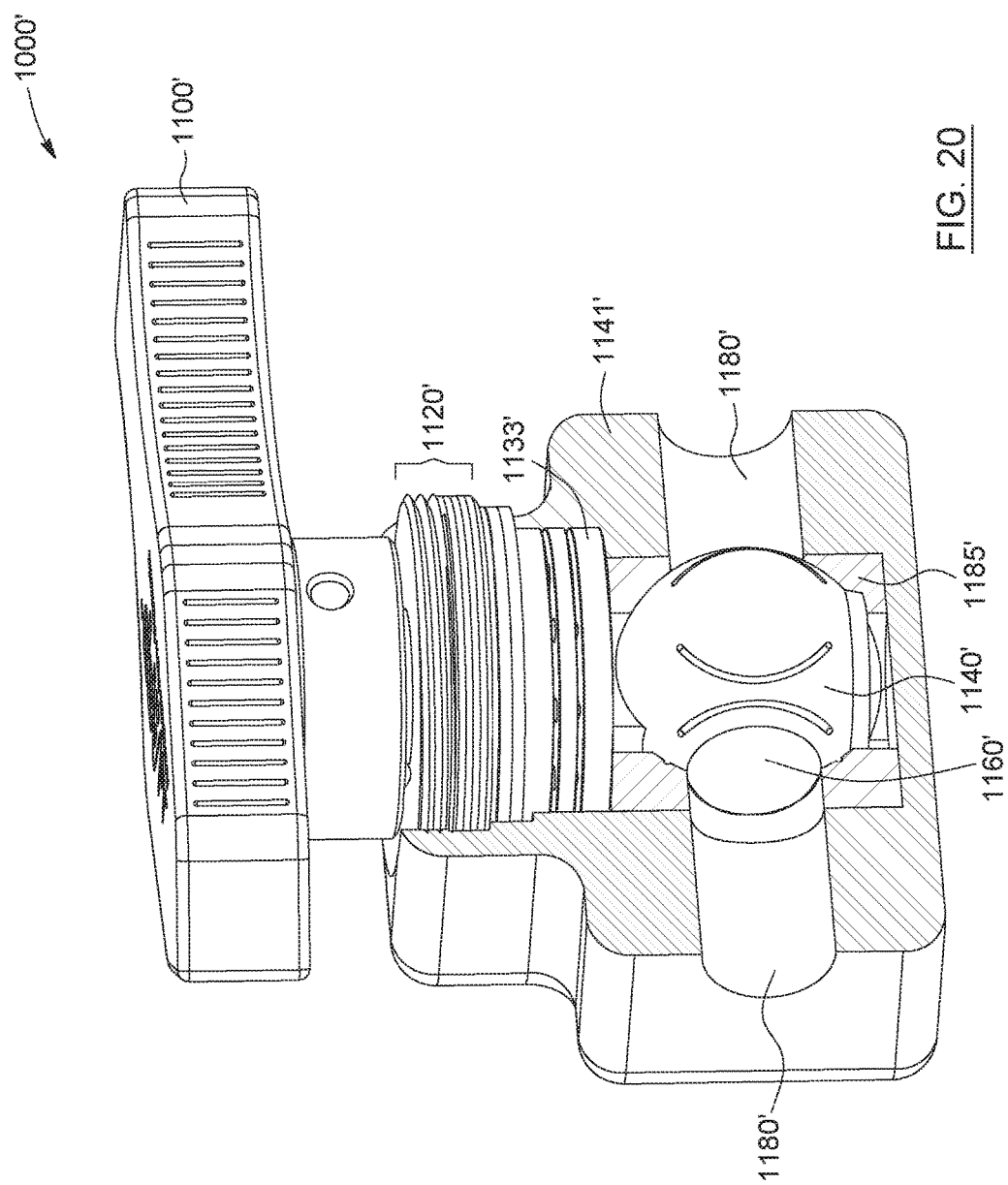
FIG. 20 is a perspective view of the rotary valve of FIG. 17, with the enclosure and packing shown in cross-section.
Figure 21:
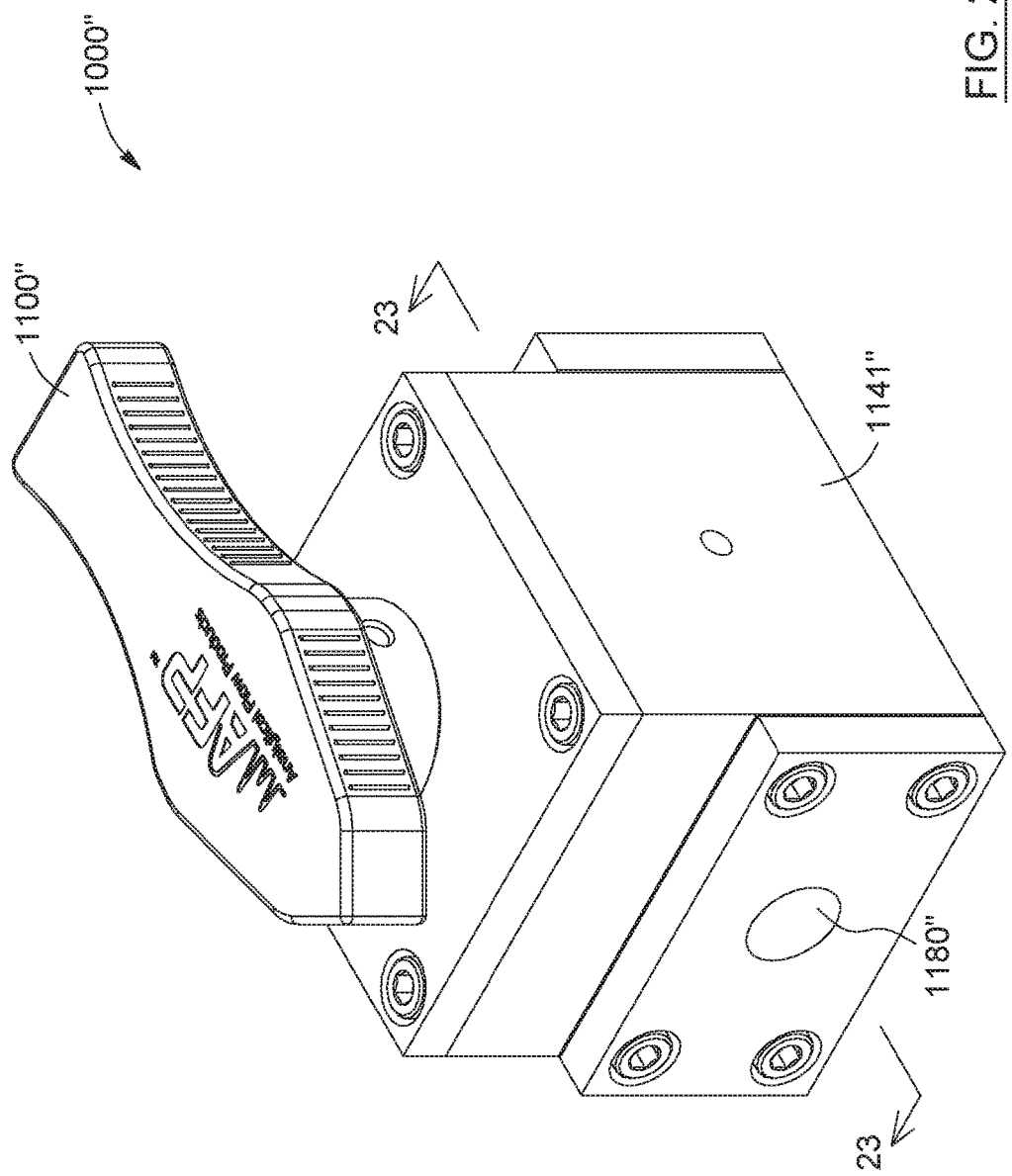
FIG. 21 is a perspective view of a rotary valve, according to a fifth implementation of the invention.

Referring now to FIGS. 17 to 19, another implementation of a ball-valve is shown. The valve 1000' is similar to the one of FIGS. 12 to 16, excepted that the geometry of parts is slightly changed. The packing 1140' is made of 2 parts, and the fixed annular plate 1122' is screwed to the valve enclosure 1141'. Compressible annular seals 1127' surround the load varying mechanism 1120'. As shown in FIGS. 19A to 19B, the load biasing mechanism is similar to the one of the valve 1000, of FIGS. 12 to 16. The mechanism 1120' includes a static member 1122' and a movable member 1121'. The movable member 1121' includes portions with sloped profiles delimited by stoppers 1125'. The static member 1122' includes sliding blocks 1129' which can slide over the sloped profile 1123'. Rotation of the shaft 1126' raises or lowers the plate 1121' relative to the static plate 1122', thereby varying the height of the biasing element 1130', which in turn varies the load applied by the biasing element on the valve element 1160'.

Finally, referring to FIGS. 21, 22 and 23A-23B, another implementation of a ball valve is provided. This valve 1000" mainly differs from the other two valves 1000 and 1000' because it includes a second mechanism which seals the packing and ball interfaces in a direction orthogonal to the sealing load force applied by the biasing element 1130". The biasing or spring assembly 1130" can thus be referred to as a first spring assembly which biases the ball 1160" axially, or vertically, toward the packing 1140".

The valve 1000" includes a second spring assembly 1137" which biases the packing 1140" towards the ball 1160" in a radial, or lateral, direction. The valve 1000" also includes a load transfer mechanism 1300" operatively linked to the movable member 1121" of the load varying mechanism 1120", for varying the load force applied on the second biasing assembly 1137" proportionally to the load force applied by the first spring assembly 1130".

More specifically, in the present case, the second spring assembly 1137" is disposed outside of the packing and surrounds the fluid passages. The load transfer mechanism 1300" includes a fixed plate 1304" and a slidable plate 1302" disposed axially, or vertically, relative to the enclosure. The plate 1032" is operatively connected, and in this case in direct contact with, the second spring assembly 1137". The plates 1302" and 1304" have mating inclined surfaces. The transfer mechanism 1300" also includes a rod 1139" disposed between the movable member 1121" of the load varying mechanism 1120" and the slidable plate 1302" of the load transfer mechanism 1300".

Figure 23B:
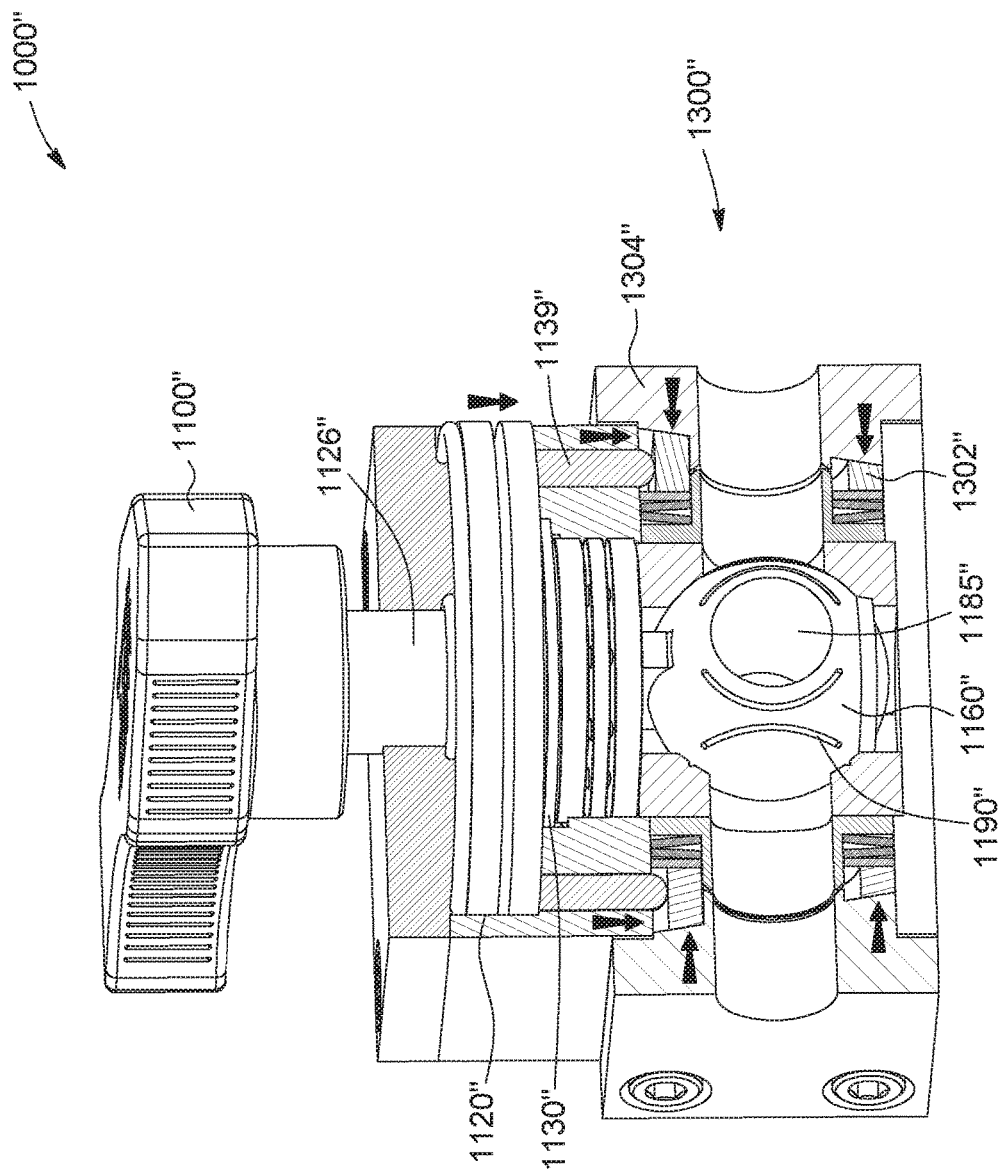
FIG. 23B is a perspective view of the rotary valve of FIG. 21, with the stator shown in cross-section, in a configuration where fluid communication is prevented between two ports, the rotor being stationary.
Figure 24:
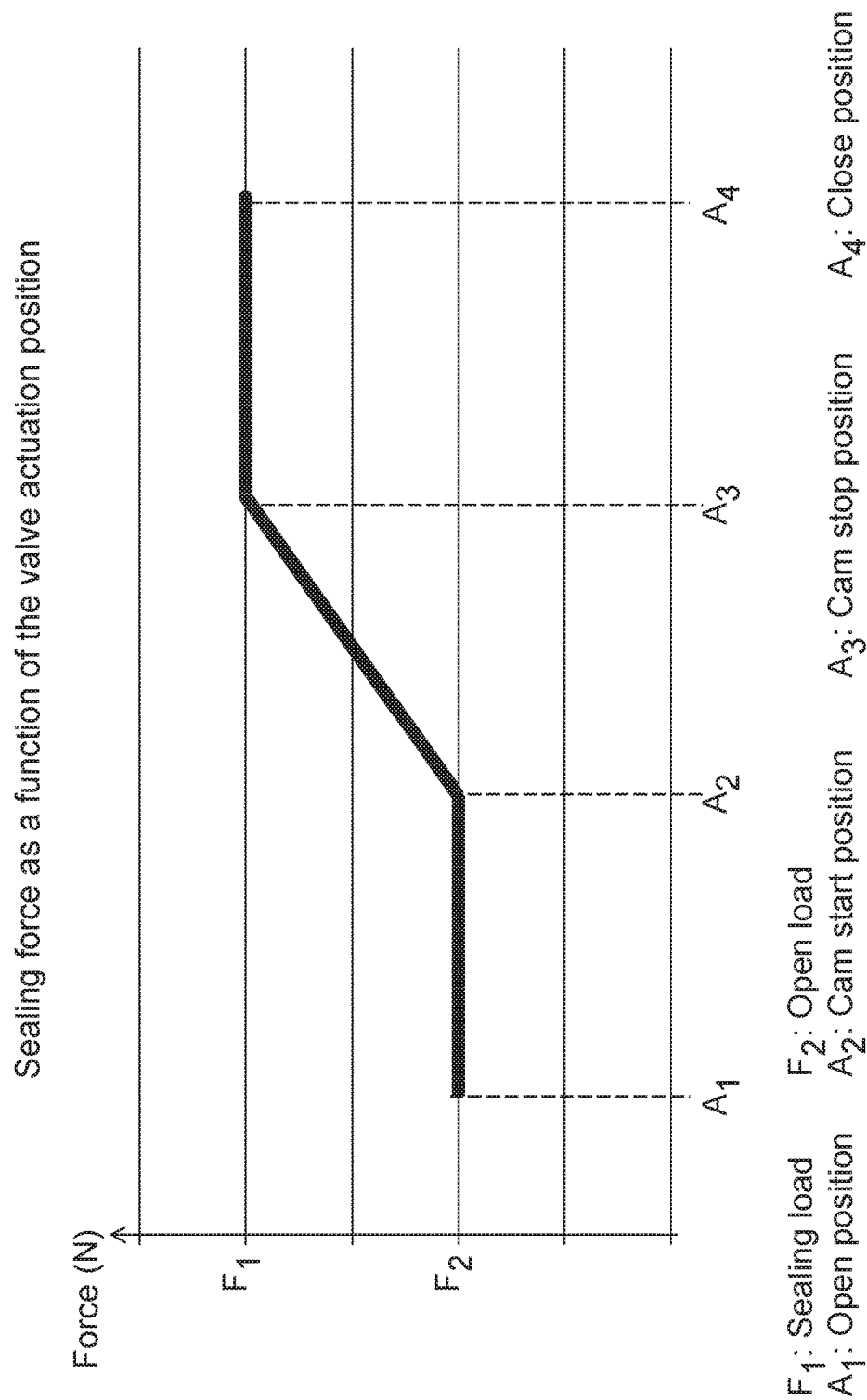
FIG. 24 is a graph of showing the sealing load force applied as a function of positions of the valve element.
Figure 25A:
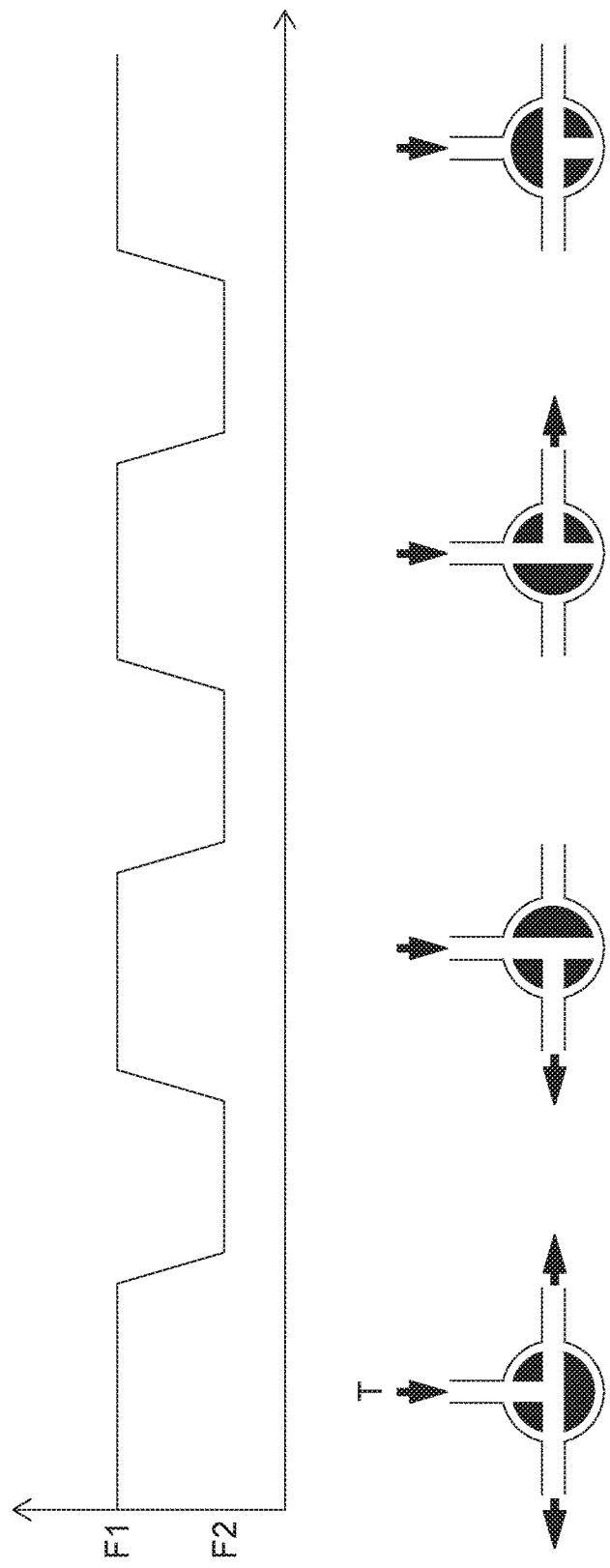

Upon rotation of the shaft 1126", such as shown in FIG. 23B, the movable member 1121' is lowered for compressing the first spring assembly 1130". The rod 1139" is forced downwardly, pushing the slidable plate 1302". The plate 1302" can move thanks to springs located on each side of the plate 1302'. Because of its slanted or inclined profile, the plate 1302" moves downwarly and laterally, towards the ball 1160", when the biasing assembly 1130" is compressed. When moving towards the ball 1160" the plate 1032" compresses the second spring assembly 1137" radially, further increasing sealing of the packing and the ball.

Of course, although the two different implementations of the actuating system presented are respectively electromechanical and mechanical, other types of actuating systems can be used, such as pneumatic, hydraulic, magnetic, etc.

An advantage of the method and valves above, is that they require less torque to be operated, especially for the implementation presented in FIG. 4. Another advantage is that the pressure applied on the valve element does not depend upon the pressure required for the application process. In other word, the pressure applied on the valve element of the valve by the biasing element and load varying mechanism is completely independent from the pressure used in the analytical system, or of the force of the motor used to rotate the rotor.

Of course it can be considered to use the process fluid to apply the loading force on the rotor; however, in this case the pressure of the fluid used for applying on the rotor is controlled independently from the pressure used in the analytical process. The method described in the present application is applicable to different types of valve, including conical valve, ball valves and sliding valves.

As can be appreciated, the method, actuating system and rotary valve described herein allow lowering the loading force applied on the rotor during its rotation, so as to reduce friction between the rotor and stator sealing surfaces. Reducing said friction diminishes in turn wear of the sealing surfaces, increasing the lifetime of the valve.

Of course, numerous modifications could be made to the implementations described above without departing from the scope of the present invention.

The invention claimed is:

1. A valve for channeling a fluid therethrough, the valve comprising:
   a static body provided with fluid passages for circulating the fluid therein at a fluid pressure, the body having a body interface with ports connected to said fluid passages;
   a valve element having a valve element interface facing the body interface, said valve element interacting with the ports of the body interface, the valve element being movable between different positions so as to permit or obstruct communication between the fluid passages;
   an actuating mechanism for moving the valve element between the different positions;
   a spring assembly configured to bias the valve element interface against the body interface with a sealing load force; and
   a load varying mechanism configured to variably load the spring assembly based on the different positions of the valve element,
   the spring assembly applying a first sealing load force when the valve element is stationary and a second sealing load force when the actuating assembly moves the valve element between the different positions, the second sealing load force being smaller than the first sealing load force, while being sufficient to maintain sealing contact between the body interface and the valve element interface.

2. The valve according to claim 1, wherein the load varying mechanism comprises:
   a first motor for variably compressing the spring assembly;
   a controller controlling the first motor;
   a position sensor connected to the controller and operatively linked to the valve element, to detect the different positions of the valve element and to send the detected positions to the controller;
   the position sensor detecting the different positions of the valve element and sending the detected positions to the controller, the controller controlling the first motor based on the detected positions received, the first motor compressing and decompressing the spring assembly, the spring assembly applying a sealing force equal or between the first and second sealing forces on the valve element based on the position of the valve element.

3. The valve according to claim 2, comprising a second motor for moving the valve element, the second motor moving the valve element between the different positions, the second motor being connected to the controller.

4. The valve according to claim 2, comprising a temperature sensor to detect operating temperatures of the valve and to send the temperatures detected to the controller, the controller controlling the first motor for compressing or decompressing the spring assembly according to the operating temperatures detected by the temperature sensor.

5. A valve according to claim 1, wherein the actuating mechanism comprises a rotatable shaft operatively coupled to the valve element, the load varying mechanism comprising a mechanical assembly including a movable member and a static member, the movable member being operatively coupled to the rotatable shaft, the rotatable shaft moving the valve element between the different positions and also moving away or bringing closer the movable member relative to the static member, thereby compressing or decompressing the spring assembly.

6. The valve according to claim 5, wherein the body has a cavity bordered by a sidewall, said sidewall comprising the body interface, the valve element is a rotor disposed within the cavity, said rotor having at least one channel opening on the valve element interface for interacting with the ports of body interface, the rotor being rotatable between the different positions so as to permit or obstruct communication between the fluid passages via the at least one channel.

7. The valve according to claim 6, wherein the static and movable members of the load varying mechanism are first and second cam washers having respective inner faces at least partially contacting one another, said inner faces including concave and convex portions, and wherein applying the first sealing load force is obtained by positioning the rotatable shaft such that the respective convex portions of the cam washers are in contact, thereby compressing the spring assembly, and applying the reduced sealing load force is obtained by positioning the rotatable shaft such that the respective convex and concave portions are mated, thereby decompressing the spring assembly and reducing the load force applied on the rotor.

8. The valve according to claim 6, wherein the static and movable members are plates disposed within the static body, the plates having respective inner faces at least partially contacting each other, one of said inner faces having at least one portion with a sloped profile, the inner face of the other plate having at least one sliding block configured to slide along the sloped profile, whereby rotating the shaft forces the sliding block to slide along the sloped profile, thereby compression or decompressing the spring assembly.

9. The valve according to claim 8, wherein the plate having at least one portion with the sloped profile comprises at least two stoppers delimiting said portion with the sloped profile, the stoppers limiting movement of the sliding block therebetween.

10. The valve according to claim 9, wherein said at least one portion with the sloped profile also comprises two flat portions disposed on each side of the sloped profile, between the at least two stoppers.

11. The valve according to claim 6, wherein:
the body is a housing having top and bottom ends;
the rotor has a frustro-conical body with a narrow end and a wide end, the rotor fitting within said cavity with the narrow end disposed at the top end of the body, the at least one channel consisting in at least one groove disposed at the surface of the frustro-conical body,
the rotatable shaft is connected to the narrow end of the frustro-conical body and extends outwardly of the housing top end;
the load varying mechanism is disposed at the wider end of the frustro-conical body; and
the spring assembly is disposed beneath the load varying mechanism;
said conical rotary valve comprising a disk at the bottom end of the housing, compressing the spring assembly and closing off the cavity.

12. The valve according to claim 6, wherein the body is a packing comprising the cavity, the rotor is a ball fitting within the cavity, and the at least one channel is a through hole extending within the ball, the valve comprising an enclosure having top and bottom sides, the enclosure housing the packing and the ball, the rotatable shaft having a first end connected to the ball and a second end extending outside of the packing, on one of the top and bottom sides of the enclosure; the load varying mechanism and the spring assembly being disposed above the packing, within the enclosure.

13. The valve according to claim 12, wherein the spring assembly is a first spring assembly biasing the ball axially toward the packing, the valve further comprising:

a second spring assembly for biasing the packing towards the ball in a radial direction; and a load transfer mechanism operatively linked to the movable member of the load varying mechanism, for varying the load force applied on the second biasing assembly proportionally to the load force applied by the first spring assembly.

14. The valve according to claim 13, wherein the second spring assembly is disposed outside of the packing and surrounds the fluid passages; the load transfer mechanism comprises:

a fixed plate and a slidable plate extending axially relative to the enclosure, the movable plate being operatively connected to the second spring assembly, said plates having mated inclined surfaces; and a rod disposed between the movable member of the load varying mechanism and the slidable plate, whereby when the movable member of the load varying mechanism is lowered for compressing the first spring assembly, the rod pushes the slidable plate of the load transfer mechanism downwardly which in turn compresses the second spring assembly radially, further increasing sealing of the packing and the ball.

15. The valve according to claim 1, wherein the spring assembly applies a sealing load force with an intermediate sealing load force value when the valve element moves past the ports of the static body, the intermediate sealing load force having a value between a process sealing force value corresponding to the first sealing load force and a movement sealing force value applied in between two successive ones of said ports and corresponding to the second sealing load force.

16. The valve according to claim 15, wherein the spring assembly is compressible to different sizes for applying the different load sealing forces.

17. The valve according to claim 15, wherein the load varying mechanism comprises a movable member, for compressing or decompressing said spring assembly, the movable member being linked to the valve element.

18. The valve according to claim 15, wherein the load varying mechanism is a mechanical assembly operatively linked to the spring assembly.

* * * * *

UNITED STATES PATENT AND TRADEMARK OFFICE
CERTIFICATE OF CORRECTION

PATENT NO. : 10,428,960 B2
APPLICATION NO. : 15/231149
DATED : October 1, 2019
INVENTOR(S) : Yves Gamache It is certified that error appears in the above-identified patent and that said Letters Patent is hereby corrected as shown below:

In the Specification

Column 2, Line 57:
"in" should be — is —

Column 3, Line 2:
"the" should be — to —

Column 3, Line 36:
After "height" insert -- of --

Column 3, Line 57:
"to" should be — two —

Column 4, Line 20:
After "to" insert -- a --

Column 6, Line 14:
"passages" should be — passage —

Column 6, Line 20:
After "fluid" insert -- is --

Column 6, Line 51:
"time" should be — times —

Column 7, Line 23:
Delete "allows"

Signed and Sealed this
Third Day of March, 2020

Andrei Iancu
*Director of the United States Patent and Trademark Office*

Column 7, Line 40:
"a" should be — an —

Column 7, Line 53:
"volts" should be — volt —

Column 8, Line 47:
After "softening" insert -- of --

Column 8, Line 52:
"analyses" should be — analysis, —

Column 8, Line 53:
"need" should be — needs —

Column 9, Line 4:
"analysed" should be — analyzed —

Column 10, Line 41:
After "prior" insert -- to --

Column 10, Line 48:
"as" should be — a —

Column 11, Line 38:
"portions" should be — portion —

Column 11, Line 41:
"material" should be — materials —

Column 11, Line 43:
"in" should be — is —

Column 12, Line 7:
"material" should be — Material —

Column 12, Line 14 (second occurrence):
After "with" insert -- a --

Column 12, Line 19:
"area" should be — areas —

Column 12, Line 61:
After "contact" insert -- with --

CERTIFICATE OF CORRECTION (continued)
U.S. Pat. No. 10,428,960 B2

Column 13, Line 3:
"30" should be — 130 —

Column 13, Line 3:
Delete "are" (second occurrence)

Column 13, Line 7:
"affect" should be — affects —

Column 13, Line 14:
"in" should be — of —

Column 13, Line 34:
"in" should be — In —

Column 13, Line 38:
"127" should be — 129 —

Column 13, Lines 39, 40:
"Hr, Hr. . . Hs" should be — HR, HR . . . HS —

Column 14, Line 1:
"cam washers" should be — cam-washers —

Column 14, Line 4:
"H" should be — HS —

Column 14, Line 18:
"cam washers" should be — cam-washers —

Column 14, Line 20:
"H" should be — HS —

Column 14, Line 24:
"cam washers" should be — cam-washers —

Column 14, Line 28:
"cam washer" should be — cam-washer —

Column 14, Line 33:
"it" should be — is —

Column 14, Line 39:
"Ts" should be — TS —

Column 14, Line 47:
"LFs" should be — LFS —

Column 14, Line 50:
"of" should be — to —

Column 15, Line 1:
"in" should be — of —

Column 15, Line 3:
"ball valve" should be — ball-valve —

Column 15, Line 30:
Delete "is"

Column 15, Line 40:
"members" should be — member —

Column 15, Line 61:
"1121" (second occurrence) should be — 1122 —

Column 16, Line 3:
"slide" should be — slides —

Column 16, Line 5:
"1121" (second occurrence) should be — 1122 —

Column 16, Line 20:
"130" should be — 1130 —

Column 17, Line 6:
"1121'" should be — 1121" —

Column 17, Line 10:
"1302'" should be — 1302" —

Column 17, Line 25:
"word" should be — words —

Column 17, Line 32:
After "applying" insert -- force --

Column 17, Lines 35, 36:
"valve" should be — valves —

In the Claims

Column 18, Claim 2, Line 11:
After "motor;" insert -- and --

Column 18, Claim 7, Lines 54, 59:
"cam washers" should be — cam-washers —

Column 19, Claim 8, Line 6:
"compression" should be — compressing —

Column 19, Claim 11, Line 21:
"in" should be — of —